(12) United States Patent
Takeuchi et al.

(10) Patent No.: US 10,702,714 B2
(45) Date of Patent: Jul. 7, 2020

(54) RADIATION THERAPY SYSTEM

(71) Applicant: HITACHI, LTD., Tokyo (JP)

(72) Inventors: Keigo Takeuchi, Tokyo (JP); Yuji Ichinose, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 210 days.

(21) Appl. No.: 15/563,089

(22) PCT Filed: Apr. 13, 2016

(86) PCT No.: PCT/JP2016/061851
§ 371 (c)(1),
(2) Date: Sep. 29, 2017

(87) PCT Pub. No.: WO2016/181744
PCT Pub. Date: Nov. 17, 2016

(65) Prior Publication Data
US 2018/0071548 A1    Mar. 15, 2018

(30) Foreign Application Priority Data

May 14, 2015 (JP) .................................. 2015-098688

(51) Int. Cl.
*A61N 5/10* (2006.01)
*A61B 6/10* (2006.01)
(Continued)

(52) U.S. Cl.
CPC .............. *A61N 5/107* (2013.01); *A61B 6/107* (2013.01); *A61B 6/547* (2013.01); *A61N 5/1031* (2013.01);
(Continued)

(58) Field of Classification Search
CPC .... A61N 5/107; A61N 5/1039; A61N 5/1081; A61N 5/1049; A61B 6/542; A61B 6/107;
(Continued)

(56) References Cited

U.S. PATENT DOCUMENTS 5,299,250 A    3/1994    Stymol et al.
6,307,914 B1   10/2001   Kunieda et al.
(Continued)

FOREIGN PATENT DOCUMENTS

JP    06-7343 A      1/1994
JP    07-092587 A    4/1995
(Continued)

OTHER PUBLICATIONS

Translation JP 2006-122448 (Year: 2006).*
(Continued)

*Primary Examiner* — Yara B Green
(74) *Attorney, Agent, or Firm* — Mattingly & Malur, PC

(57) ABSTRACT

An object is to provide a radiation therapy system which can easily and accurately set an X-ray irradiation range. A movable X-ray diaphragm unit 6 has, in its configuration, an X-ray shielding unit configured with a plurality of members, a driver for the X-ray shielding unit, and a position detector for acquiring a position of the X-ray shielding unit. It has displays 8 and 9 which display a transmission image of a subject based on an output of an X-ray detection unit and a simulation image when the X-ray shielding unit is projected on the X-ray detection unit 2 based on an output of the position detector.

6 Claims, 14 Drawing Sheets

(51) Int. Cl.
*A61B 6/00* (2006.01)
*A61B 6/06* (2006.01)

(52) U.S. Cl.
CPC ......... *A61N 5/1049* (2013.01); *A61N 5/1065* (2013.01); *A61N 5/1067* (2013.01); *A61B 6/06* (2013.01); *A61B 6/4014* (2013.01); *A61B 6/4441* (2013.01); *A61N 5/1038* (2013.01); *A61N 5/1075* (2013.01); *A61N 2005/1059* (2013.01); *A61N 2005/1061* (2013.01)

(58) Field of Classification Search
CPC ........... A61B 6/547; A61B 6/106; A61B 6/54; A61B 6/06
See application file for complete search history.

(56) References Cited

U.S. PATENT DOCUMENTS

| | | | | |
|---|---|---|---|---|
| 6,379,041 B1 * | 4/2002 | Schuetz | ................. | A61B 6/547 378/205 |
| 6,435,716 B1 * | 8/2002 | Polkus | ................. | A61B 6/4233 378/197 |
| 9,480,437 B2 * | 11/2016 | Watanabe | ............... | A61B 6/022 |
| 2009/0080618 A1 * | 3/2009 | Kosugi | .................... | A61B 6/04 378/146 |
| 2012/0076275 A1 * | 3/2012 | Ida | ....................... | A61B 6/4233 378/98.8 |
| 2013/0237810 A1 * | 9/2013 | Iwai | ....................... | A61B 5/061 600/424 |

FOREIGN PATENT DOCUMENTS

| | | |
|---|---|---|
| JP | 2000-167072 A | 6/2000 |
| JP | 2006-87660 A | 4/2006 |
| JP | 2006-122448 A | 5/2006 |
| JP | 2012-070984 A | 4/2012 |
| JP | 2013-215654 A | 10/2013 |

OTHER PUBLICATIONS

Translation of JP H10-344423 (Year: 2000).*
Translation of JP 2012-070984 (Year: 2014).*
Translation H07-092587 (Year: 1995).*
Translation of JP 2004-276574 (Year: 2006).*
International Search Report of PCT/JP2016/061851 dated Jul. 19, 2016.

* cited by examiner

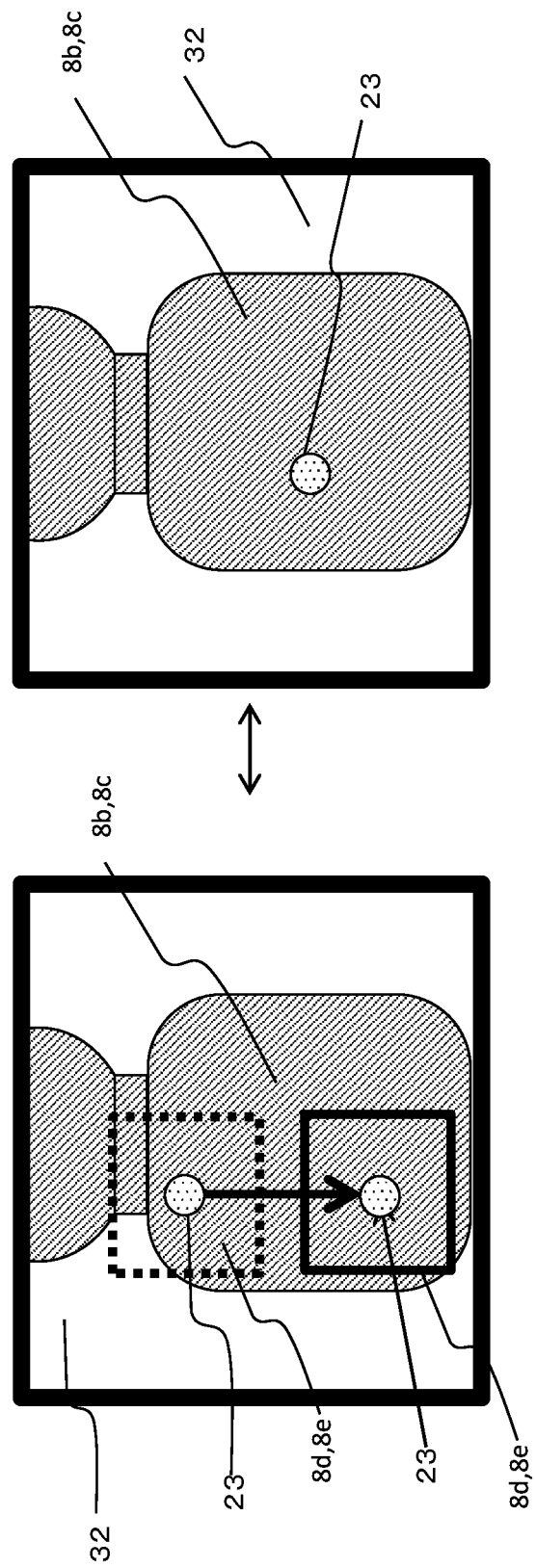

RADIATION THERAPY SYSTEM

TECHNICAL FIELD

The present invention relates to a radiation therapy system which includes particularly an X-ray imaging device.

BACKGROUND ART

In a therapy radiation therapy system with high accuracy, for example, an X-ray radiation system with high accuracy or a particle therapy system, a known one is one using X-ray irradiation for accurately specifying a position of a target volume.

When X-ray photography is performed for a subject, to avoid unnecessary X-ray exposure or deterioration in image quality, an X-ray diaphragm is provided between an X-ray tube and an X-ray detection unit, and a controller controlling the position of each blade of the X-ray diaphragm is operated, thereby setting the X-ray irradiation range.

In the conventional X-ray diaphragm, there is provided a potentiometer outputting a voltage in accordance with displacement of a drive motor to the drive motor connected to each blade. Thus, before X-ray imaging, an opening state of the X-ray diaphragm does not need to be in an initial state, and a target position of the blade is set in relation to the current position of the blade which has been detected by the potentiometer, thereby setting the X-ray irradiation range. This technique is disclosed in Patent Literature 1.

CITATION LIST

Patent Literature

Patent Literature 1: Japanese Unexamined Patent Application Publication No. 2013-215654

SUMMARY OF INVENTION

Technical Problem

However, in the conventional X-ray diaphragm, the position of each blade has been controlled by operating a controller installed independently from a monitor, for setting an X-ray tube output condition or displaying an imaged image.

However, to set an appropriate X-ray irradiation range 6a, an X-ray needs to be irradiated to a subject. It has been difficult to set the irradiation range 6a without irradiation. Imaging conditions including the tube voltage and the X-ray irradiation range 6a are different among patients. Thus, an imaging condition needs to appropriately be set for every X-ray imaging, and it has been difficult to set the X-ray irradiation range 6a to the minimum when a moving target is imaged. It is therefore an object of the present invention is to provide a radiation therapy system with which an operator can easily and accurately set the X-ray irradiation range.

Solution to Problem

To solve the above problem, various preferred embodiments of the present invention can be considered. As a specific example, according to the present invention, there is provided a radiation therapy system "comprising: X-ray imaging device; radiation therapy device for irradiating radiation for treatment; and a control device which is connected to the X-ray imaging device or the radiation therapy device, wherein the X-ray imaging device has an X-ray generation unit, an X-ray detection unit which detects an X-ray irradiated from the X-ray generation unit, thereby acquiring a transmission image of a subject, and a movable X-ray diaphragm unit which adjusts an irradiation range of an X-ray irradiated from the X-ray generation unit, the movable X-ray diaphragm unit has, in its configuration, an X-ray shielding unit which is configured with a plurality of members, driver for the X-ray shielding unit, and position detector for acquiring a position of the X-ray shielding unit, and the control device has display for displaying the transmission image of the subject based on an output of the X-ray detection unit and a simulation image when the X-ray shielding unit based on an output of the position detector is projected on the X-ray detection unit."

Advantageous Effects of Invention

According to the present invention, there is provided a radiation therapy system with which an operator can easily and accurately set an X-ray irradiation range.

BRIEF DESCRIPTION OF DRAWINGS

FIG. 14 is a matching process image diagram in the X-ray imaging included in the moving body tracking radiation therapy system according to the third embodiment of the present invention.

DESCRIPTION OF EMBODIMENTS

First Embodiment

Figure 1:
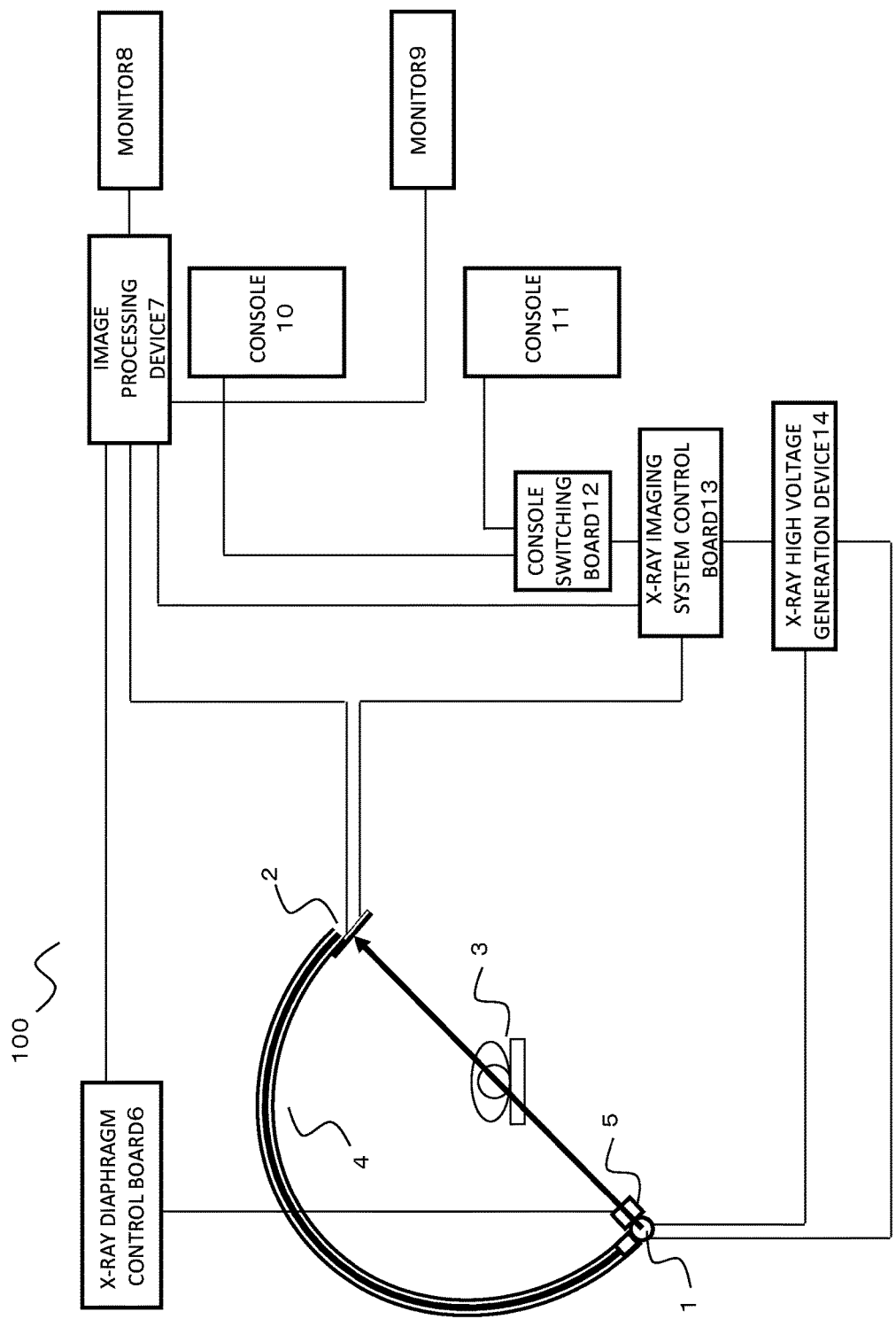
FIG. 1 is a diagram illustrating the entire configuration of an X-ray imaging device according to a first embodiment of the present invention.

FIG. 1 is a configuration diagram of an X-ray imaging device 100.

The X-ray imaging device 100 includes an X-ray tube 1 which irradiates an X-ray to a subject 3, an X-ray high voltage generation device 18 which applies a high voltage to an X-ray tube for irradiating X-rays, an X-ray diaphragm 5 which restricts an irradiation range 6a of the X-rays, an X-ray detection unit 2 which detects a penetrating X-ray of the subject 3 arranged oppositely to the X-ray tube 1, a C-arm 4 which rotates the X-ray tube 1 and the X-ray detection unit 2 around the subject 3, an image processing device 7 which processes an image acquired by the X-ray detection unit 2, a console switching board 12 which realizes a remote operation for two rooms in which monitor 8 or 9 and consoles 10 and 11 are provided, in association with each room, and an X-ray imaging system control board 13 which entirely controls the X-ray imaging system.

The X-ray imaging device 100 of this embodiment has the X-ray diaphragm 5, which restricts the irradiation range 6a of the X-ray tube 1 and can change the size or form of the imaging range.

Figure 3:
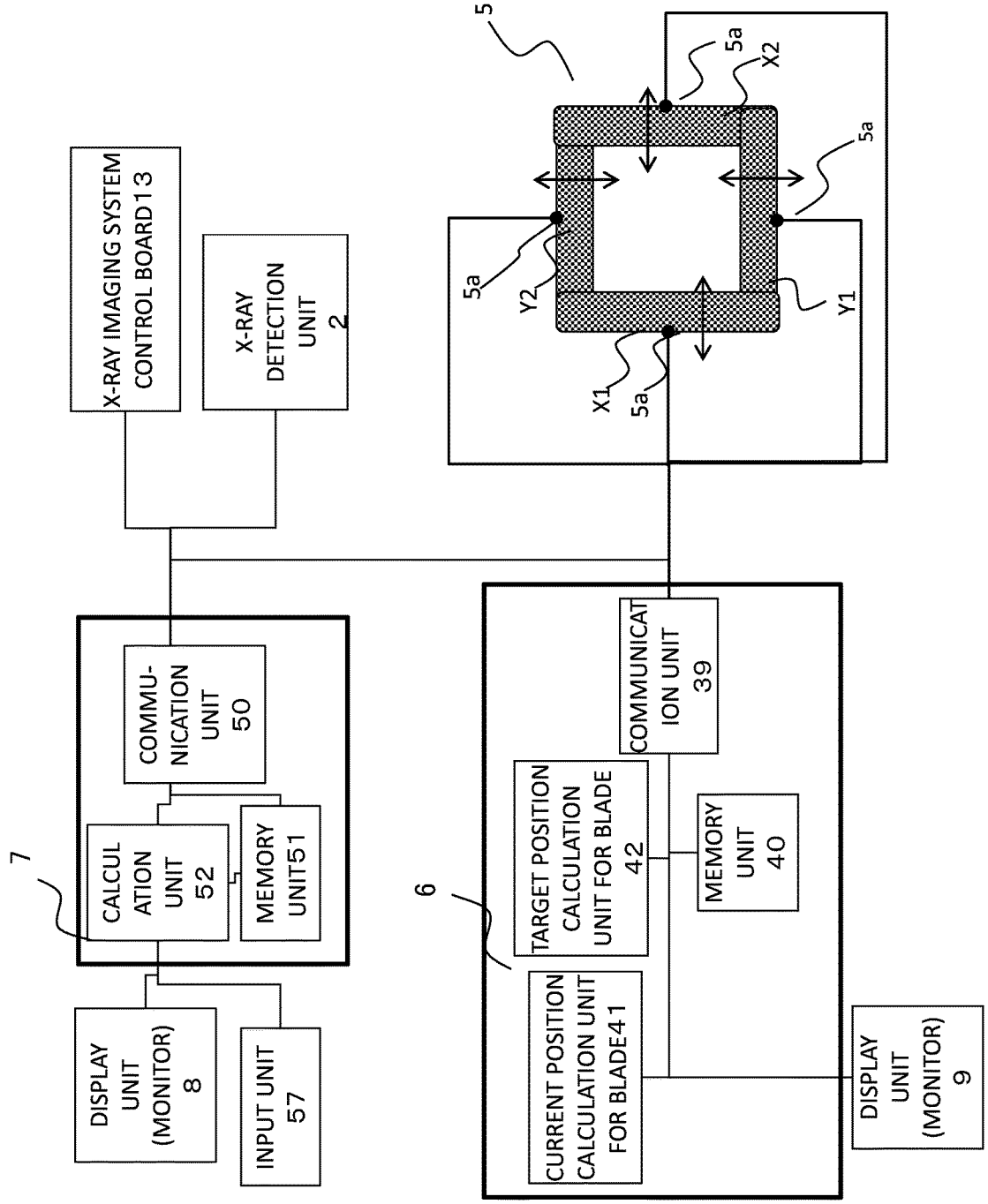
FIG. 3 is a control block diagram of an X-ray imaging device according to the first embodiment of the present invention.

FIG. 3 is a block diagram illustrating, together with a related device, a functional configuration of each of the X-ray diaphragm 5, an X-ray diaphragm control board 6, and an image processing device 7, in this embodiment.

The X-ray diaphragm 5 has, as illustrated in FIG. 3, has four blades X1, X2, Y1, and Y2 and drive motors (not illustrated) driving these blades. Each of the blades is formed of a material having a high X-ray absorption coefficient, and can be formed of using, for example, aluminum or copper. As illustrated in FIG. 2(a), a potentiometer (position detection means 5a) is installed for each blade. Each potentiometer 5a outputs a voltage (a signal) in accordance with a position of each blade to a communication unit 39 of the X-ray diaphragm control board 6.

The X-ray diaphragm control board 6 has, as illustrated in FIG. 2(a) or FIG. 3, the communication unit 39 communicating with the image processing device 7 or the X-ray diaphragm 5, a memory unit 40 storing the current position coordinates or target position coordinates of the blade, a current position calculation unit 41 for the blade, a target position calculation unit 42 for the blade, and display units (monitors) 8 and 9 displaying the above calculation result, an X-ray imaged image, and a calculation result to be described later. The current position calculation unit 41 calculates the position coordinates of the blades X1, X2, Y1, and Y2 in the X-ray detection unit 2, using a voltage value received from the potentiometer 5a included in the X-ray diaphragm 5, and transmits them to the memory unit 40 of the X-ray diaphragm control board 6 or a memory unit 51 of the image processing device 7.

Note that the position of each blade in the X-ray detection unit 2, in this case, may be assumed as information regarding the position which can be acquired at the time the position coordinates of each blade are made to correspond to the outer edge of a detection area of the X-ray on the X-ray detection unit 2 when a radially-irradiated X-ray is restricted by the X-ray diaphragm 5. In other words, the information may represent the position which has been projected on the X-ray detection unit 2. This position shows the position of the blade in the vicinity of the X-ray tube 1.

The target position calculation unit 42 issues an instruction for causing the current position coordinates of the blade which are received from the memory unit 40 to coincide with target position coordinates of the blade which are received from the memory unit 40, to be described later, to the drive motor connected to each blade.

The image processing device 7 has, as illustrated in FIG. 3, a communication unit 50, the memory unit 51, a calculation unit 52, and the display units (monitors) 8 and 9. The communication unit 50 communicates with the X-ray diaphragm control board 6 or the X-ray detection unit 2, and the X-ray imaging system control board 13. The memory unit 51 stores an imaging condition, including an output of the X-ray tube 1, such as a tube voltage, and an X-ray imaging condition such as the position of the C-arm 4 in association with each patient. The calculation unit 52 calculates the target position (the X-ray irradiation range 6a) of each blade which is set by the operator on the monitor 8 or 9, as the target position coordinates of the blade on the X-ray detection unit 2, using various methods to be described later, and transmits them to the memory unit 40 of the X-ray diaphragm control board 6 through the communication unit 50. The display units 8 and 9 display a target position instruction for the blade, to be described later, or the calculation result.

Upon reception of the current position coordinates of the blade in the X-ray detection unit 2 from the memory unit 40 of the X-ray diaphragm control board 6, the image processing device 7 displays the current position of each blade on the monitor 8 or 9. With a display method, it is possible to display the current position coordinates of the blade as a numerical value, or to simulate the X-ray irradiation range 6a in the X-ray detection unit 2 and display it on the monitor 8 or 9, by converting the blade's position or size in the X-ray diaphragm 5, as illustrated in FIG. 2(b), into the position or size in the screen size of the monitor 8 or 9. The operator specifies the target position of the blade, while checking the current position coordinates of the blade which are displayed on the monitor 8 or 9 or the simulated and displayed X-ray irradiation range 6a.

Figure 4:
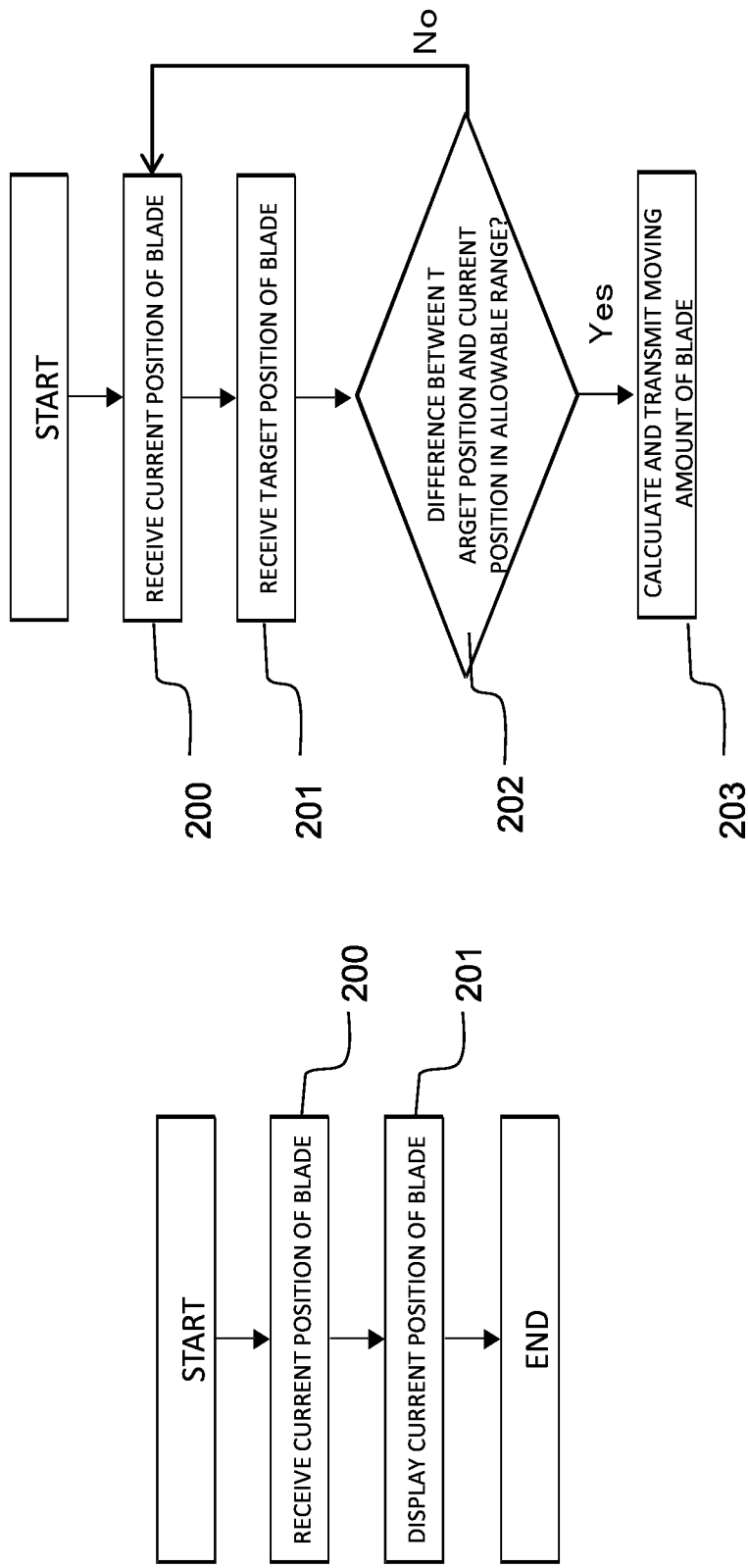
FIG. 4 is a diagram illustrating a control flow of the X-ray diaphragm in the first embodiment of the present invention.

Descriptions will now be made to control procedures of the X-ray diaphragm control board 6 and the image processing device 7 in this embodiment, using FIG. 4. FIG. 4 is a flowchart illustrating the contents of a control process of the X-ray diaphragm control board 6 in this embodiment.

In Step 200, the current position calculation unit 41 calculates the position coordinates of each of the blades X1, X2, Y1, and Y2 in the X-ray detection unit 2, using a voltage value received from the potentiometer included in the X-ray diaphragm 5, and transmits them to the memory unit 40.

After this, it proceeds to Step 201, and the calculation unit 52 of the image processing device 7 calculates the target position (the X-ray irradiation range 6a) of each blade which is set by the operator on the monitor 8 or 9, as the target position coordinates of the blade in the X-ray detection unit 2, and transmits it to the memory unit 40 of the X-ray diaphragm control board 6.

After this, it proceeds to Step 202, the X-ray diaphragm control board 6 determines whether the current position coordinates of each blade are equal to the target position coordinates, based on information recorded in the memory unit 40. In Step 202, when the target position coordinates are equal to the current position coordinates, the operation of the blade is to be completed. In Step 202, when the target position coordinates are not equal to the current position coordinates, the flow proceeds to Step 203. It calculates a moving amount of the blade that the target position of the blade is equal to the current position, and transmits the moving amount of each blade to the X-ray diaphragm 5. In this case, when the target position calculation unit 42 transmits the moving amount of each blade to the X-ray diaphragm 5, the operator may set the moving speed for each of the blades X1, X2, Y1, and Y2, on the monitor 8 or 9.

After this, back to Step 200, the memory unit 40 of the X-ray diaphragm control board 6 receives the current position coordinates and the target position coordinates of each blade, and the X-ray diaphragm control board 6 continuously determines whether the target position of the blade is equal to the current position. Note that this comparison determination between the target position and the current position is executed by the target position calculation unit 42 or the current position calculation unit 41, or another calculation unit (not illustrated).

A set of control loop procedures which are formed from Step 200 to Step 203 are executed based on a calculation cycle which is arbitrarily set for the X-ray diaphragm board 6. Thus, the current position of the blade, the target position, and the moving amount are updated as needed, based on the calculation cycle. However, this control is only one example. Even if the target position coordinates are changed during the movement of the blade, it is not necessary to immediately update them. It is possible to provide a mode for movement toward the target position coordinates acquired by calculation, after the blade has reached the previously received target position coordinates. This calculation has been executed right after this arrival.

The number of blades is not necessarily four, and may, for example, be eight. The blades may have a different X-ray absorption coefficient. The position detection of the blades is not necessarily performed by the potentiometer. For, example, an encoder may be used as position detection means. The current position coordinates of each blade in the X-ray detection unit 2 and the moving amount of each blade can be calculated by the X-ray diaphragm control board 6, the image processing device 7, or the X-ray imaging system control board 13. However, in this specification, the calculations are to be performed by the X-ray diaphragm control board 6. The current position coordinates of each blade and the target position coordinates on the X-ray detection unit 2, the moving amount of each blade, and various settings including the moving speed can be performed also by the X-ray diaphragm control board 6, the image processing device 7, or the X-ray imaging system control board 13.

In this embodiment, there are given a plurality of methods for the operator to specify the target position of the blade on the monitor 8 or 9. The operator can control the position of each blade, by selecting or combining any of the blade's various control modes stored in the memory unit 40 of the X-ray diaphragm control board 6 or the memory unit 51 of the image processing device 7.

Figure 2:
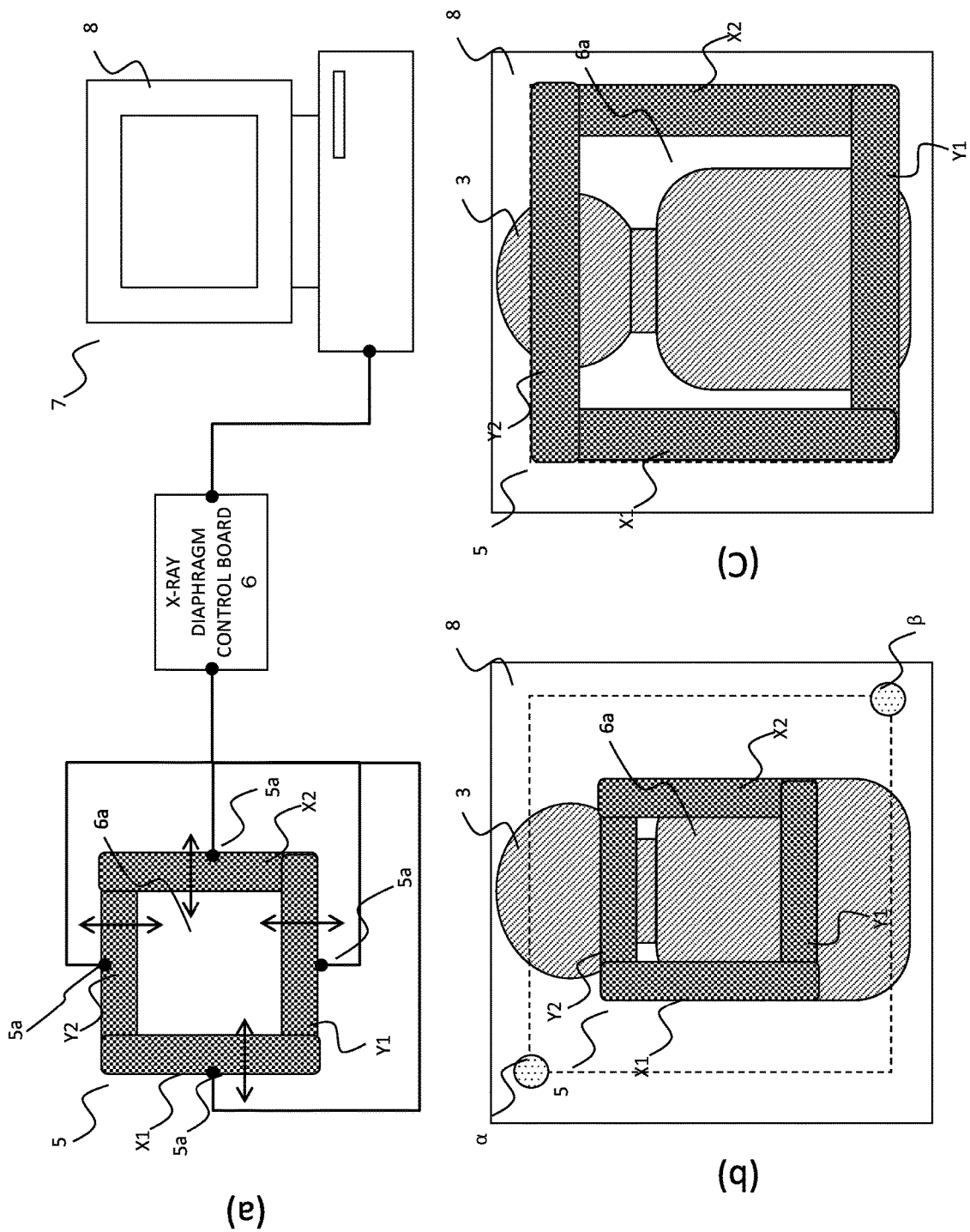
FIG. 2 is a control block diagram of an X-ray diaphragm in the first embodiment of the present invention, and is a display example in a display unit and an operation example through the display unit.

For example, it is not necessary that the target position (the X-ray irradiation range 6a) of the blade is specified by the operator on the monitor 8 or 9 using the coordinates. As illustrated in FIG. 2(*b*), if the operator specifies two points α and μ on the monitor 8 or 9, as illustrated in FIG. 2(*c*), it can be considered that the image processing device 7 obtains the X-ray irradiation range 6a having a rectangle which is illustrated with a dotted line. This rectangle has a line segment connecting the points using a straight line, as a diagonal line. At this time, the calculation unit 52 of the image processing device 7 calculates the target position coordinates of each blade on the X-ray detection unit 2 based on the two points specified on the monitor. It is also possible to select a mode (a first mode) for transmitting them to the X-ray diaphragm control board 6.

By selecting the first mode, the operator can easily specify the X-ray irradiation range 6a. Even without X-ray irradiation, the X-ray irradiation range 6a of the X-ray diaphragm 5 can be checked, and its size can appropriately be controlled in response to an input instruction through the monitor. Thus, the X-ray imaging device of this embodiment can reduce an irradiation amount of the X-ray, as compared with the conventional X-ray imaging device which acquires information regarding the X-ray irradiation range 6a by the X-ray irradiation.

For example, the operator in advance stores a predetermined value as a moving amount in the unit of each blade, in the memory unit 40 of the X-ray diaphragm control board 6, and selects the side of "OPEN" or "CLOSE" on the monitor 8 or 9, for each of the blades X1, X2, Y1, and Y2 displayed or displayed by simulation on the monitor 8 or 9. Then, in this case, it is possible to select a mode (a second mode) for moving the position of each blade by a certain moving amount which is set in advance for a selected direction.

In this control mode, if the side of "OPEN" or "CLOSE" is selected on the monitor 8 or 9, in relation to each of the blades X1, X2, Y1, and Y2 displayed or displayed by simulation on the monitor 8 or 9, the target position calculation unit 42 issues an instruction for the current position coordinates of the blade received from the memory unit 40 to move in the selected direction (the side of OPEN or CLOSE) by the stored certain moving amount, to the X-ray diaphragm 5.

By selecting the second mode, the operator specifies the side of OPEN or CLOSE for the blade's position displayed or displayed by simulation on the monitor 8 or 9, thereby easily and accurately setting the X-ray irradiation range 6a to the minimum and attaining a reduction in an exposure dose of patients.

While the operator specifies the side of OPEN or CLOSE in relation to the position of the blades X1, X2, Y1, and Y2 displayed or displayed by simulation on the monitor 8 or 9, it is also possible to select a mode (a third mode) for continuously moving the blade in the specified direction. In this control mode, the certain moving amount of the blades is stored in advance in the target position calculation unit 42, while the side of OPEN or CLOSE is selected on the monitor 8 or 9 in relation to the blades X1, X2, Y1, and Y2 displayed or displayed by simulation on the monitor 8 or 9, and the stored certain moving amount is transmitted to the X-ray diaphragm 5 in relation to the current position coordinates of the blades received from the memory unit 40.

By selecting the third mode, the operator can continuously move the blade to the side of OPEN or CLOSE in relation to the position of each blade displayed on the monitor 8 or 9, can easily cause the X-ray irradiation range 6a to follow a moving target, and can attain a reduction in the exposure dose of the patients.

To realize that the positions of the right and left blades X1 and X2 or the positions of the upper and lower blades Y1 and Y2 are respectively in symmetrical positions or in vertically symmetrical positions with respect to the center of the X-ray detection unit 2, the target position calculation unit 42 of the X-ray diaphragm control board 6 can also select a mode (a fourth mode) for controlling the positions of the blades X1, X2, Y1, and Y2. Descriptions will now be made to a controlling method in the control mode, by way of example, as a case for controlling the positions of the symmetrical blades X1 and X2 to be in symmetrical positions with respect to the center of the X-ray detection unit 2.

Upon reception of the target position coordinates of the blade from the calculation unit 52 of the image processing device 7, the target position calculation unit 42 for the blade included in the X-ray diaphragm control board 6 calculates a moving amount based on the target position coordinates of a predetermined blade, and outputs it as a moving amount of each blade. A method can be considered in which even without setting a predetermined blade as a standard for calculating the moving amount, a difference between the target position coordinates and the current position coordinates is obtained in association with each blade, and one moving amount of each blade is set, based on the maximum value and the minimum value. This control may be applied to the movement of not only the right and left blades, but also the upper and lower blades.

By selecting the fourth mode, when a slice image is reconfigured into a three-dimensional image at the time of performing, for example, CBCT (cone beam CT) imaging, it is possible to reduce the non-uniformity (asymmetry) of the image. As a result, it is possible to attain a reduction in the exposure dose of patients.

The memory unit 40 of the X-ray diaphragm 6 stores in advance the relationship between the positions of the blades which are detected by the potentiometer included in the X-ray diaphragm 5 and differences with the actual positions of the blades. The current position calculation unit 41 for the blade displays the position of each blade on the monitor 8 or 9, and the target position calculation unit 42 for the blade transmits the target position coordinates for the blade to the X-ray diaphragm 5. At this time, it is possible to select a mode (a fifth mode) for the image processing device 7 or the X-ray diaphragm control board 6 to automatically correct the differences. By selecting the fifth mode, it is possible to reduce a stop error of each blade due to a quantization error of the potentiometer, and to attain a reduction in the exposure dose of patients.

When, for example, the image processing device 7 or the X-ray diaphragm control board 6 controls each blade to operate to the target position, it is possible to select a mode (a sixth mode) for controlling each blade to operate to the target position from a fully opened state or a fully closed state. By selecting the sixth mode, by controlling each blade to operate always from the fully opened state to the target position, it is possible to reduce a stop error of each blade due to a quantization error of the potentiometer or hysteresis, and to attain a reduction in the exposure dose of patients.

When, for example, the image processing device 7 reconfigures a slice image to a three dimensional image at the time of CBCT imaging, it is also possible to select a mode (a seventh mode) for reconfiguring the three dimensional image based on the current position of the blade which has been received from the potentiometer. That is, the three dimensional image is reconfigured using an image which has been corrected by extracting a non-effective region (a region not for use in reconfiguration of the three dimensional image) of the slice image. By selecting the seventh mode, it can be expected that quality of the three dimensional image is improved, and it is possible to reduce generation of an artifact at the time of reconfiguring the image. This results in reducing the risk of re-imaging, and attaining a reduction in the exposure dose of patients.

For example, it is possible to select a mode for the X-ray imaging system control board 13 to control the X-ray tube 1, in a manner that the X-ray imaging device 100 allows irradiation of an X-ray only when the entire blades X1, X2, Y1, and Y2 stop at the target positions.

In this control mode, the memory unit 40 transmits a signal for permitting the X-ray imaging system control board 13 to perform irradiation of an X-ray, only when there is a coincidence between the coordinates of the blades which are calculated by the current position calculation unit 41 for the blade and the coordinates which are calculated by the target position calculation unit 42 for the blade. When there is a change in the position of any of the blades X1, X2, Y1, and Y2 during X-ray imaging, that is, when there is no coincidence between the coordinates of the blades which are calculated by the current position calculation unit 41 for the blade and the coordinates calculated by the target position calculation unit 42 for the blade, the memory unit 40 transmits a signal for the X-ray imaging system control board 13 to stop irradiation of an X-ray.

When, for example, X-ray CT imaging is stopped due to a position change of the blades X1, X2, Y1, and Y2 in the X-ray CT imaging, it is possible to select also a mode for restarting the X-ray CT imaging on the same X-ray imaging condition (the rotation angle of the C-arm 4, the position of the blade, or an output of the X-ray tube 1) as that at the point that the imaging is stopped.

In this control mode, the memory unit 40 of the X-ray diaphragm control board 6, the memory unit 51 of the image processing device 7, or the X-ray imaging system control board 13 stores the X-ray imaging condition. After the X-ray CT imaging is stopped, at the time the X-ray CT imaging is restarted, the same X-ray imaging condition as that at the point the imaging is stopped is automatically set for each device.

For example, after the X-ray diaphragm control board 6 transmits the target positions X1, X2, Y1, and Y2 of the blades X1, X2, Y1, and Y2 to the X-ray diaphragm 5, it is possible to select a mode for detecting an error when the blade has not reached the target position within a time arbitrarily set by the operator and for displaying it on the monitor 8 or 9. In this control board, the time to detect a timeout error is stored in the memory unit 40 of the X-ray diaphragm control board 6. Further, when there is no coincidence between the coordinates of the blade which are calculated by the current position calculation unit 41 for the blade and the coordinates calculated by the target position calculation unit 42 for the blade within the time, an error message is displayed on the monitor 8 or 9.

Descriptions will now be made to a working effect of this embodiment.

In the X-ray diaphragm 100 described in this embodiment, position detection means is provided for each blade of the X-ray diaphragm 5, positions of the blades X1, X2, Y1, and Y2 (X-ray irradiation range 6a) are displayed by simulation on the monitor 8 or 9, and the operator specifies the X-ray irradiation range 6a on the monitor 8 or 9. In the X-ray imaging device 100 of this embodiment, there are given a plurality of methods with which the operator specifies the target position of the blade on the monitor 8 or 9, the memory unit 40 of the X-ray diaphragm control board 6 or the memory unit 51 of the image processing device 7 can control the position of the blade, by selecting or combining any of various control modes for the blade. Even without irradiation of the X-ray, the X-ray imaging device 100 of this embodiment can check the X-ray irradiation range 6a with an opening shape in the X-ray diaphragm 5, and can control appropriately its size in response to an input instruction through the display screen monitor. Thus, the X-ray imaging device of this embodiment can reduce the irradiation amount of the X-ray, as compared with the conventional X-ray imaging device which acquires information regarding the X-ray irradiation range 6a with an opening shape by X-ray irradiation.

Not only adopting only one mode, but also a plurality of control modes for the blade included in the X-ray diaphragm may be implemented, and each of the modes is combined together, thereby enabling to further improve the operability. For example, the first mode, the third mode, and the sixth mode may be combined to possibly form the following operation control.

The operator selects the first mode as a control mode for the blade through the screen of the monitor 8 or 9. The operator specifies two points on the screen, and executes approximate specification of the X-ray irradiation range 6a. At this time, a rectangular range having a line segment as a diagonal line connecting the two points is assumed as a temporary X-ray irradiation range 6a.

The operator selects the third mode through the screen of the monitor 8 or 9, and switches the control mode for each blade from the first mode to the third mode. The operator can easily and accurately set the necessary minimum X-ray irradiation range 6a by specifying the side of "OPEN" or "CLOSE" of each blade position displayed by simulation on the monitor 8 or 9.

Further, in combination with the sixth mode, it is possible to automatically correct differences between the actual positions of the blades and the positions of the blades X1, X2, Y1, and Y2 which are detected by the potentiometer included in the X-ray diaphragm 5. Thus, it is possible to easily and accurately set the X-ray irradiation range 6a.

For example, when the X-ray CT imaging is stopped due to a position change in the blades X1, X2, Y1, and Y2 in the X-ray CT imaging, the operator can easily and accurately set the necessary minimum X-ray irradiation range 6a, by using a combination of any of the modes. The modes include a mode for restarting the X-ray CT imaging on the same X-ray imaging condition (the rotation angle of the C-arm 4, the position of the blade, or an output of the X-ray tube 1) as that at the point that the imaging is stopped, a mode for continuously moving the blade in a specified direction, while the operator specifies the size of OPEN or CLOSE on the monitor 8 or 9, in relation to the positions of the blades X1, X2, Y1, and Y2 displayed or displayed by simulation on the monitor 8 or 9, a mode for the target position calculation unit 42 of the X-ray diaphragm control board 6 to control the positions of the blades X1, X2, Y1, and Y2 in a manner that the positions of the blades X1, X2, Y1 and Y2 are in symmetrical and vertically symmetrical positions with respect to the center of the X-ray detection unit 2, and a mode for permitting irradiation of an X-ray only when the entire blades X1, X2, Y1, and Y2 are stopped at target positions. Further, the positions of the upper, lower, right, and left blades are in symmetrical and vertically symmetrical positions with respect to the center of the X-ray detection unit 2. Thus, it is possible to realize a decrease in image quality at the end part (the end part vertical to the rotation direction of the C-arm 4) of the acquired image. This results in a reduction in the exposure dose of patients.

The combination of the above-described modes is only one example. A button for selecting any of the modes may be displayed on the monitor 8 or 9, and the operator may select an arbitrary mode. Alternatively, the X-ray imaging device may have a function incorporated for automatically performing a combination of some modes as a default mode.

Second Embodiment

Prior to the descriptions of this embodiment, descriptions will now simply be made to a radiation therapy system.

Figure 5:
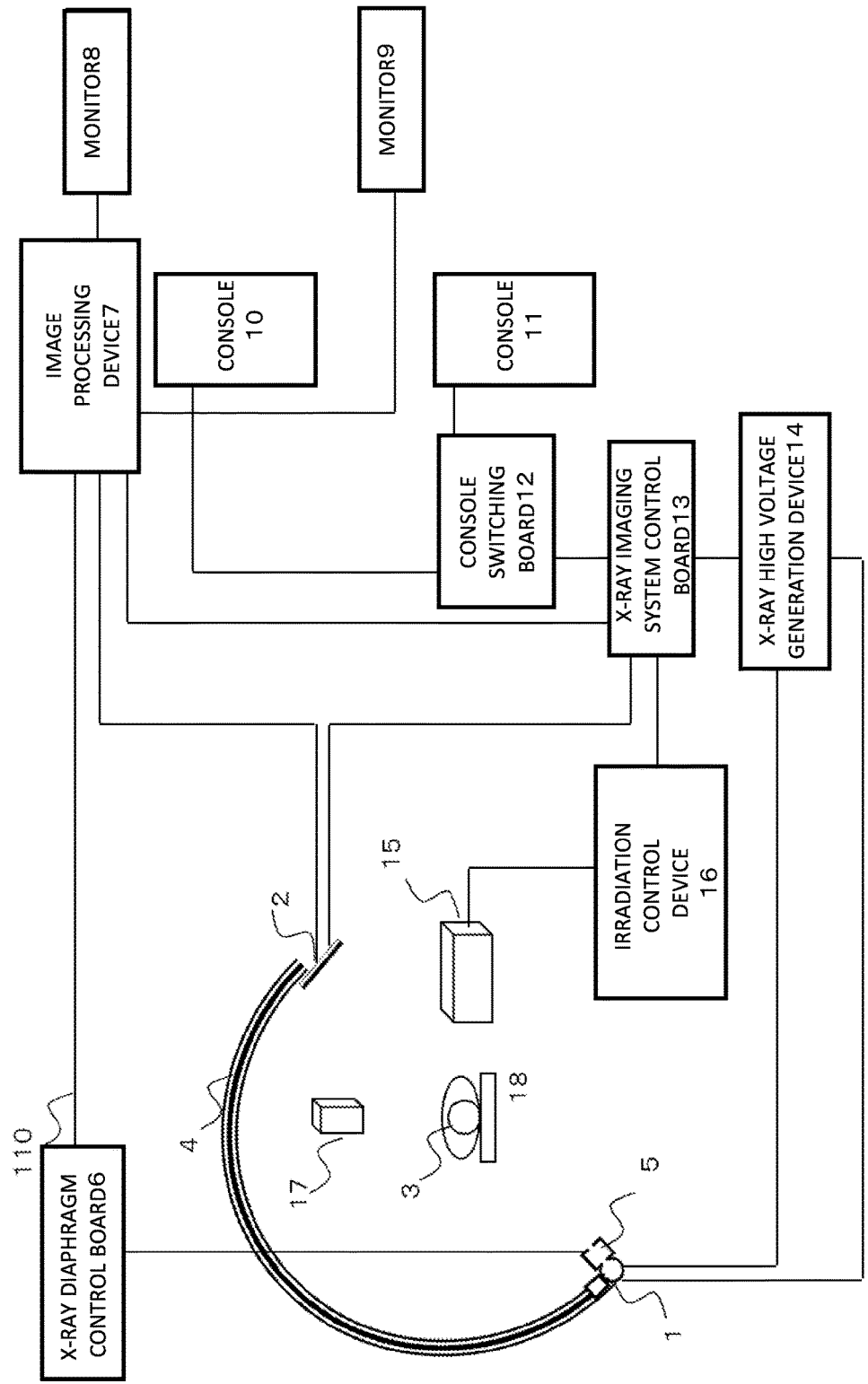
FIG. 5 is a diagram illustrating the entire configuration of a radiation therapy system according to a second embodiment of the present invention.

FIG. 5 is a schematic diagram illustrating a configuration of a radiation therapy device 110 according to this embodiment. The basic configuration is the same as the first embodiment, and the radiation therapy device includes a therapeutic radiation irradiation device 15, an irradiation control device 16, and a laser marker 17. The device 15 irradiates therapeutic radiation (for example, a high energy X-ray, an electron beam, a proton beam, a carbon beam, or any other charged particle beam) onto the subject 3 fixed on a therapy table 18. The device 16 manages entirely the radiation therapy system, including irradiation of the therapeutic radiation, the X-ray imaging, or patient information. The laser marker 17 is provided for the operator to visibly adjust the position of the radiation therapy or the position of the X-ray imaging in relation to the subject 3.

In this embodiment, the X-ray imaging device 100 described in the first embodiment is applied to the radiation therapy device 110.

In the radiation therapy device 110, the image processing device 7 displays a reference image (a therapeutic recording image) received from the irradiation control device 16 on the monitor 8 or 9. As illustrated in the first embodiment, the image processing device 7 can display the X-ray irradiation range 6a in the X-ray detection unit 2 by simulation on the monitor 8 or 9. As illustrated, the X-ray irradiation range 6a is displayed by simulation on the monitor 8 or 9, and superimposed with a reference image. The operator specifies the X-ray irradiation range 6a while checking the superimposed image. After the X-ray irradiation range 6a is determined, therapeutic radiation is irradiated, and treatment is performed, in response to an instruction of the operator.

Descriptions will now be made to control procedures or imaging procedures of the X-ray imaging system of in this function, using FIG. 6(a). FIG. 6(a) is a flowchart illustrating the contents of a control process of the X-ray diaphragm control board 6 in this embodiment.

In Step 210, the irradiation control device 16 transmits a reference image to the image processing device 7. After this, it proceeds to Step 211, and the reference image is displayed on the monitor 8 or 9. Before proceeding to Step 212, the X-ray imaging position of the subject 3 is adjusted to coincide with the imaging position of the reference image, using the laser marker 17 and the therapy table 18. After this, it proceeds to Step 212, and the X-ray irradiation range 6a is displayed by simulation on the monitor 8 or 9, and displayed in a form superimposed with the reference image displayed in Step 211. The X-ray irradiation range 6a displayed by simulation is automatically set in an appropriate range (the necessary minimum X-ray irradiation range 6a for determining the position on the patient) which is calculated by the calculation unit of the irradiation control device 16 or the image processing device 50. Note, needless to say, that the necessary minimum X-ray irradiation range 6a for determining the position may be set manually by hand.

After this, it proceeds to Step 213, the target position of the blade is specified, while checking the X-ray irradiation range 6a displayed by simulation and superimposed with the reference image. In Step 214, the X-ray imaging is performed. After this, in Step 215, the image processing device 7 causes the reference image not to be displayed, and displays the imaged image on the monitor 8 or 9.

In the conventional X-ray imaging device, the operator arbitrarily sets the X-ray irradiation range 6a which is sufficiently wide for determining the position on the patient. This results in a problem that it is difficult to reduce the exposure dose of the patients and a problem that the positioning on the patient cannot appropriately be performed due to a too small imaging range. On the contrary, in this embodiment, the calculation unit of the irradiation control device 16 or the image processing device 50 calculates the X-ray irradiation range 6a in an appropriate range, and the X-ray irradiation range 6a is automatically set. Thus, the operator can easily and accurately set the X-ray irradiation range 6a. This results in attaining a reduction in the exposure dose of the patients.

Figure 6:
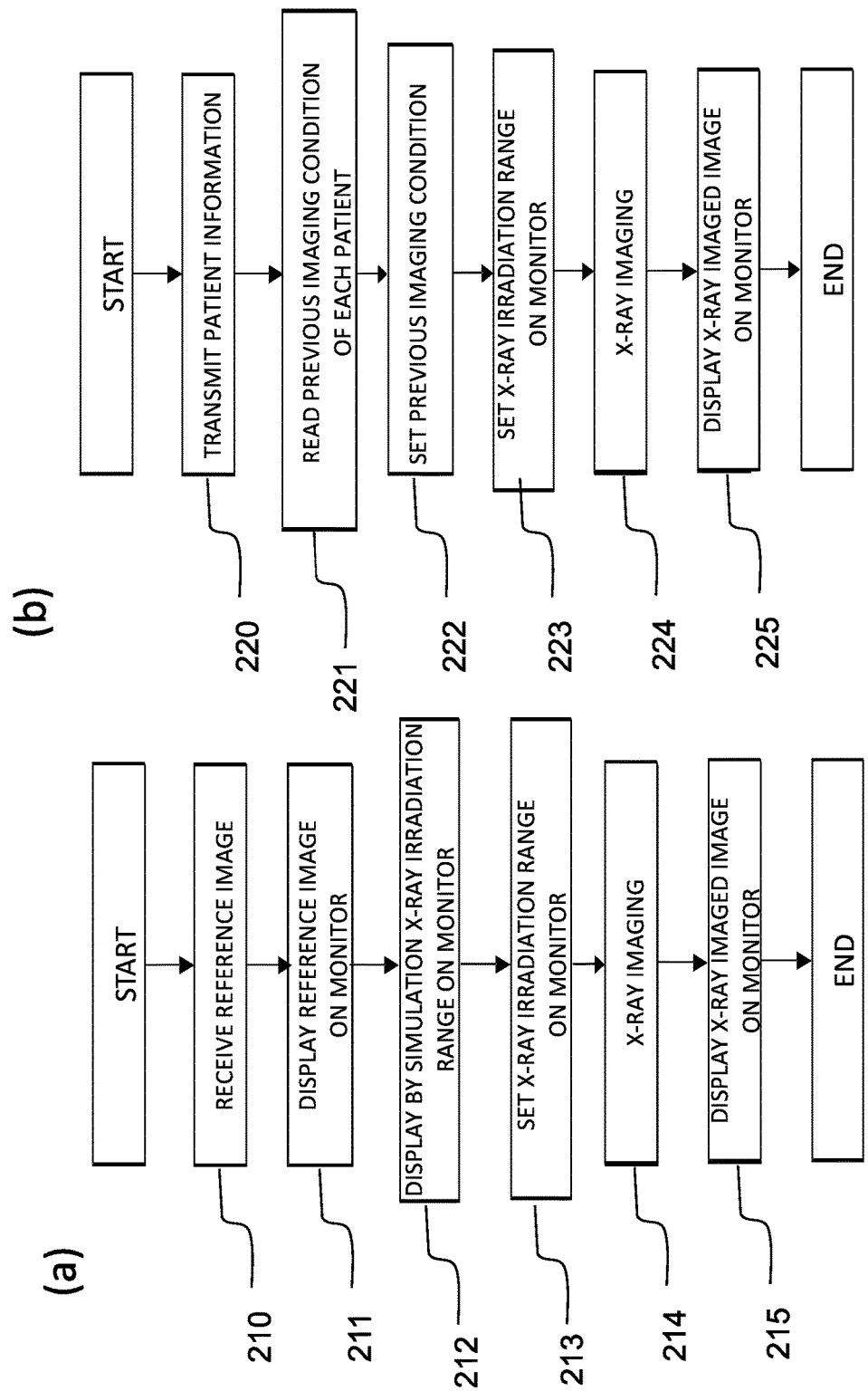
FIG. 6 is a diagram illustrating a control flow of an X-ray imaging device included in the radiation therapy system according to the second embodiment of the present invention.

In this embodiment, the memory unit 51 of the image processing device 7 stores X-ray imaging conditions which are different between patients and include the position of the blade of the X-ray diaphragm 5, the output of the X-ray tube 1, and the position of the therapy table 18. It is possible to provide a mode for automatically reading them before the next and following X-ray imaging and setting them in advance. Alternatively, it can be considered that there is a mode in which the memory unit 51 of the image processing device 7 automatically reads and sets the X-ray imaging conditions of patients. In this case, the imaging conditions are assumed to be similar to each other. Descriptions will now be made to control procedures of the X-ray imaging system in this function, using FIG. 6(*b*). FIG. 6(*b*) is a flowchart illustrating the contents of a control process of the X-ray diaphragm control board 6 in this embodiment.

In Step 220, the operator transmits patient information to the image processing device 7. After this, it proceeds to Step 221, in which the previous imaging conditions and imaged image of each patient are read. The conditions include the position of the blade of the X-ray diaphragm 5, the output of the X-ray tube 1, and the position of the therapy table 18, and are stored in the memory unit 51 of the image processing device 7. Alternatively, the memory unit 51 of the image processing device 7 automatically reads and sets the X-ray imaging conditions of the patients. In this case, the imaging conditions are assumed to be similar to each other.

After this, it proceeds to Step 222, in which the imaging conditions of the patients which are read in Step 221 are displayed on the monitor 8 or 9, and are set. On the monitor 8 or 9, the previous imaged image or reference image is displayed on the monitor 8 or 9. On the monitor 8 or 9, the operator can in advance set which of the previous imaged image and the reference image is to be displayed on the monitor 8 or 9. The memory unit 51 of the image processing device 7 can store it.

Figure 7:
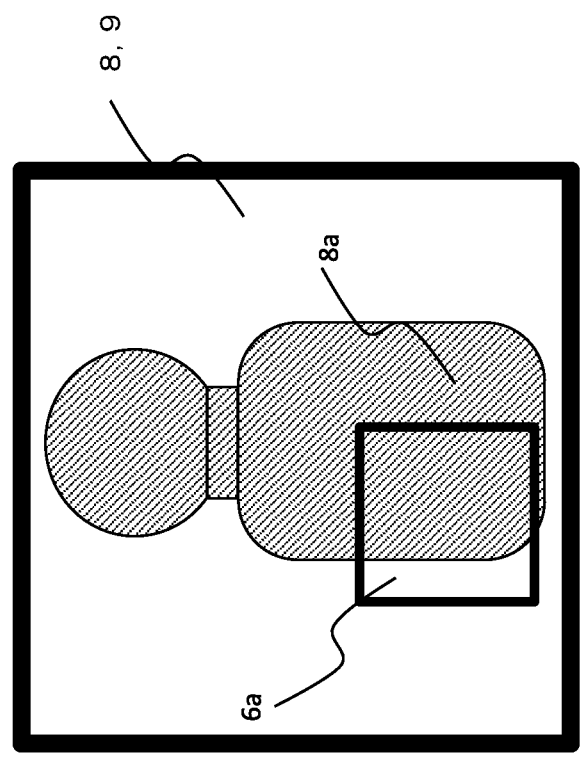
FIG. 7 is a diagram illustrating a display example in a display unit included in the radiation therapy system according to the second embodiment of the present invention.

After this, it proceeds to Step 223, and, as illustrated in FIG. 7, the X-ray irradiation range 6a is displayed by simulation on the monitor 8 or 9, and displayed in a form superimposed with a previous imaged image 8a or the reference image displayed in Step 222. In Step 223, as described in the first embodiment, the operator specifies a target position of the blade, while checking the X-ray irradiation range 6a displayed by simulation on the monitor 8 or 9. Controlling the movement of each blade is realized by any of various modes representatively including the first mode described in the first embodiment or a combination of those modes. After completion of the controlling of movement of each blade, the X-ray imaging is performed in Step 224. After completion of the imaging, in Step 225, the previous imaged image 8a or the reference image is set not to be displayed, and the imaged image is displayed on the monitor 8 or 9.

Descriptions will now be made to a working effect of this embodiment. In the X-ray imaging device 100 described in this embodiment, the X-ray imaging device 100 described in the first embodiment is applied to the radiation therapy device 110.

In this embodiment, the memory unit 51 of the image processing device 7 stores the X-ray imaging conditions which are different between patients. These conditions include the position of the blade of the X-ray diaphragm 5, the output of the X-ray tube 1, and the position of the therapy table 18. The memory unit 5 of the image processing device 7 automatically reads and sets the X-ray imaging conditions of the patients which are assumed to be similar to each other (determined by the memory unit of the image processing device 7, based on the size or the physical constitution of the target volume).

The X-ray irradiation range 6a superimposed with the reference image 8a received from the irradiation control device 16 is displayed by simulation on the monitor 8 or 9. As a result, the operator can easily and accurately specify the X-ray irradiation range 6a, while checking the superimposed image on the monitor 8 or 9.

The X-ray imaging conditions which are different between patients are stored in the memory unit 51 of the image processing device 7, and set automatically in advance before the next and following X-ray imaging. Thereby, the operator can further easily and accurately specify the X-ray irradiation range 6a.

In combination with the sixth mode (a mode for operating each blade from a fully opened state or a fully closed state to a target position, when the image processing device 7 or the X-ray diaphragm control board 6 operates the blade to the target position), it is possible to reduce a stop error of the blade due to a quantization error of the potentiometer or hysteresis, and to attain a reduction in an exposure dose of the patients.

The radiation therapy device 110 including the setting of this X-ray irradiation range 6a can reduce the exposure dose of radiation, excluding the radiation for use in therapy. This results in effects of improving the irradiation efficient of the therapeutic radiation and shortening the binding hour of the patient.

Third Embodiment

This embodiment is a moving body tracking radiation therapy device 120 into which the X-ray imaging device 100 described in the first embodiment is applied. Prior to the descriptions of this embodiment, descriptions will now briefly be made to the moving body tracking radiation therapy device.

Figure 8:
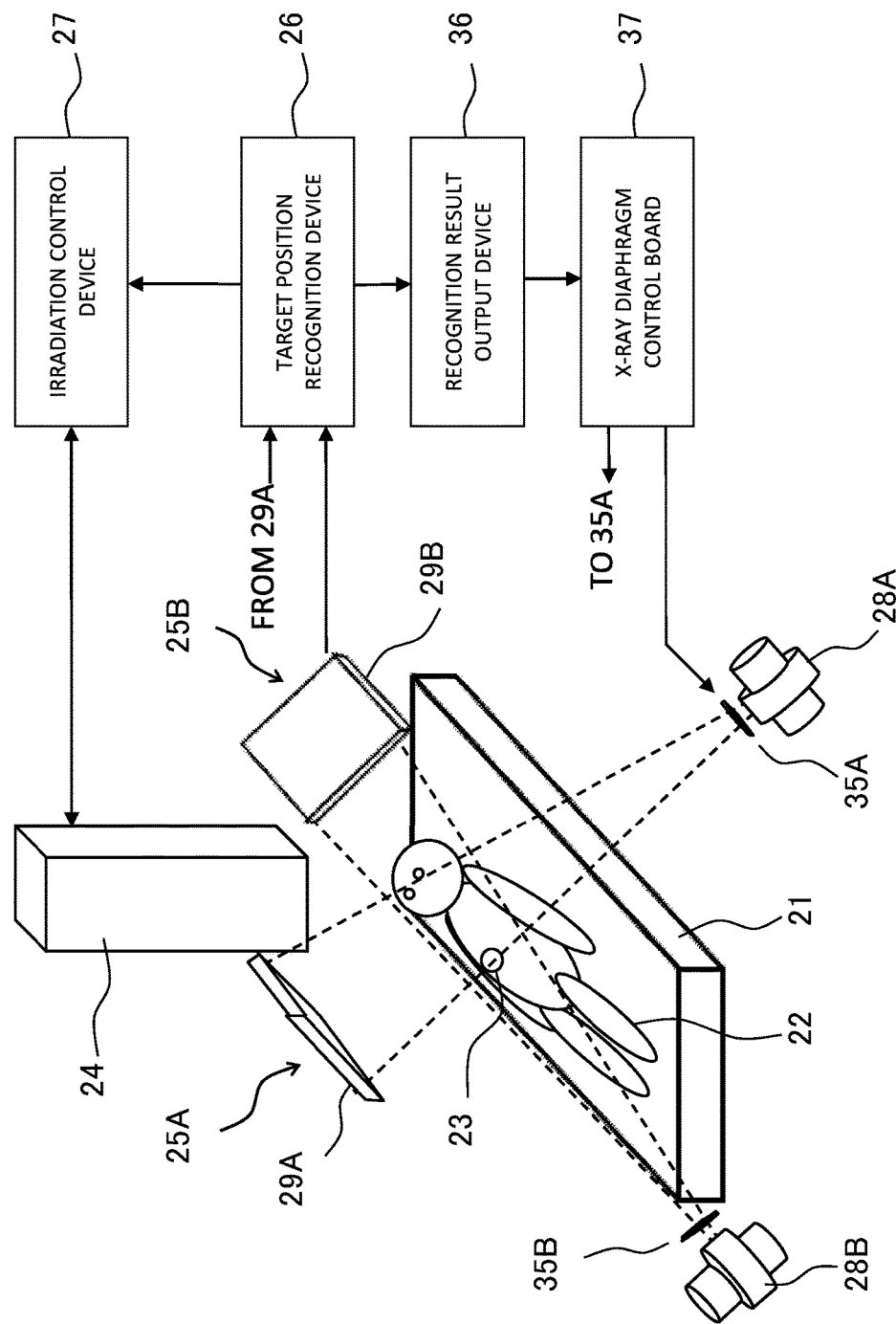
FIG. 8 is a schematic diagram of a moving body tracking radiation therapy system according to a third embodiment of the present invention.
Figure 9:
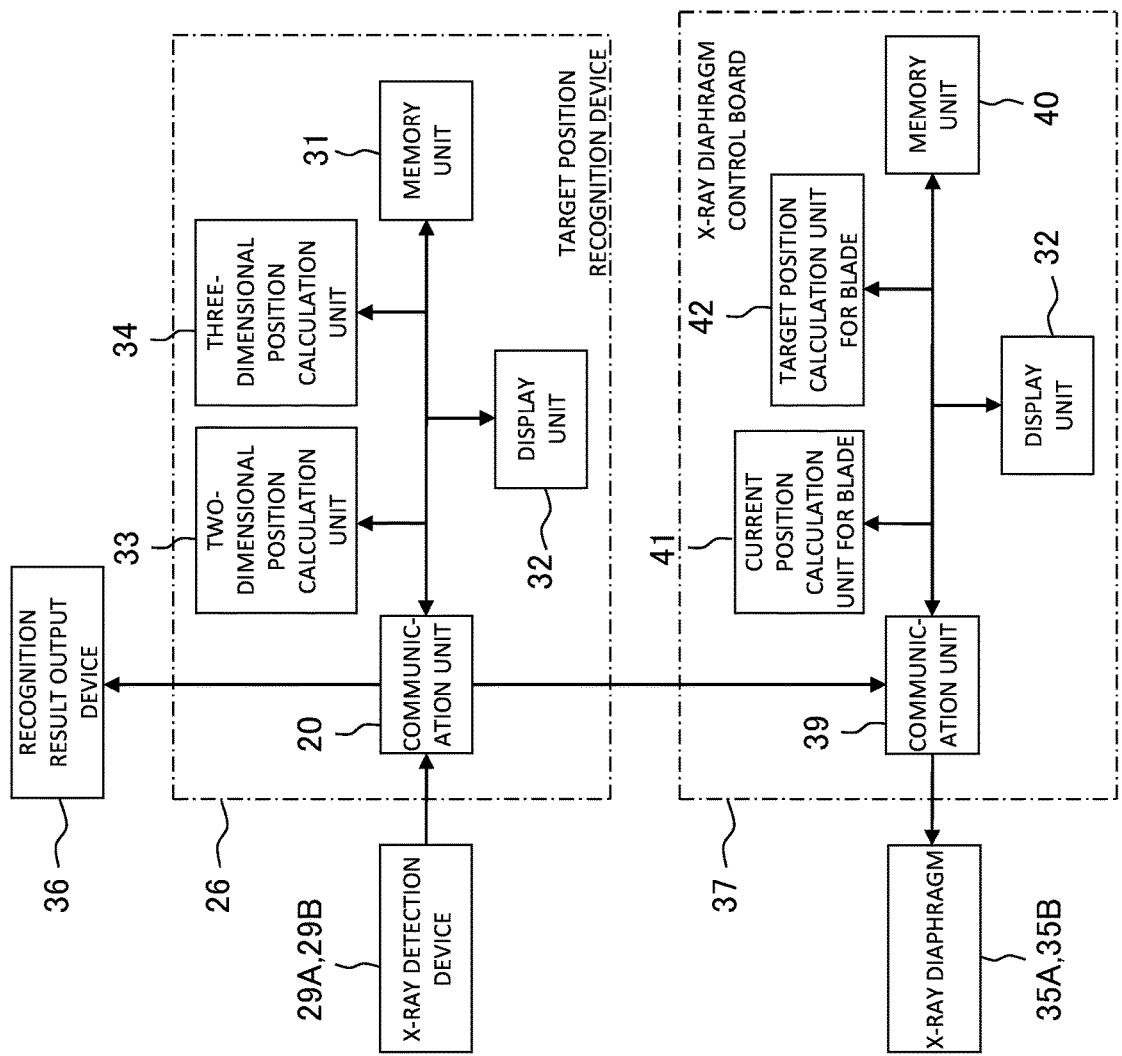
FIG. 9 is a control block diagram of an X-ray imaging device included in the moving body tracking radiation therapy system according to the third embodiment of the present invention.

FIG. 8 is a schematic diagram illustrating a configuration of the moving body tracking radiation therapy device 120 according to this embodiment. FIG. 9 is a block diagram illustrating a functional configuration of a target position recognition device and an X-ray diaphragm control board, together with related devices.

The moving body tracking radiation therapy device 120 includes a therapeutic radiation irradiation device 24, X-ray photographic devices 25A and 25B, a target position recognition device 26, and a recognition result output device 36. The device 24 irradiates therapeutic radiation (for example, a proton beam) to a target 23 in subject 22 on a therapy table 21. The devices 25A and 25B perform X-ray photography for the target 23 from a plurality of directions. The device 26 recognizes in real time the position of the target 23 using images photographed by the X-ray photographic devices 25A and 25B. The device 36 transmits the position of the target 23 which is recognized by the target position recognition device 26 to an X-ray diaphragm control board 37.

The X-ray photographic device 25A includes an X-ray tube 28A, an X-ray diaphragm 35A, an X-ray detection unit 29A, and a non-illustrative signal processing circuit. The tube 28A irradiates an X-ray to the subject 22 from a first direction. The diaphragm 35A restricts the X-ray irradiation range 6a. The unit 29A detects a two-dimensional dose distribution of an X-ray irradiated from the X-ray tube 28A and transmitted through the subject 22. The X-ray detection unit 29A has a plurality of detection elements (specifically, for example, semiconductor elements which convert radiation into electric charges) which are two dimensionally arranged, and outputs an analog signal from the detection elements. The signal processing circuit processes an analog signal from the X-ray detection unit 29A to generate data for an X-ray radioscopic image, and transmits it to the target position recognition device 26. Note that the photography by the X-ray photographic device 25A is performed at sufficient frequency (for example, approximately 30 Hz) for capturing the movement of the target 23.

Similarly, the X-ray photographic device 25B includes an X-ray tube 28B, an X-ray diaphragm 35B, an X-ray detection unit 29B, and a non-illustrative signal processing circuit. The tube 28B irradiates an X-ray to the subject 22 from a second direction (in this embodiment, a direction orthogonal to the first direction). The diaphragm 35B restricts the X-ray irradiation range 6a. The unit 29B detects a two-dimensional dose distribution of an X-ray irradiated from the X-ray tube 28B and transmitted through the subject 22. The X-ray detection unit 29B has a plurality of detection elements which are two dimensionally arranged, and outputs an analog signal from the detection elements. The signal processing circuit processes the analog signal from the X-ray detection unit 29B to generate data for an X-ray radioscopic image, and transmits it to the target position recognition device 26. Note that the photography by the X-ray photographic device 25B is performed in synchronization with the photography by the X-ray photographic device 25A.

The target position recognition device 26 includes a communication unit 20, a memory unit 31, a display unit (a monitor) 32, a two-dimensional position calculation unit 33, and a three-dimensional position calculation unit 34. The unit 20 performs communication with the X-ray photographic device 25A or 25B or an irradiation control device 27. The unit 31 stores the imaged image received from the X-ray photographic device 25A or 25B or a calculation result to be described later. The unit 32 displays the imaged image of the X-ray photographed device 25A or 25B or the calculation result to be described later. The unit 33 calculates a two-dimensional position of the target 23 viewed from a photographing direction (a first direction) of the X-ray photographic device 25A using the imaged image of the X-ray photographic device 25A, and calculates a two dimensional position of the target 23 viewed from a photographing direction (a second direction) of the X-ray photographic device 25B using the imaged image of the X-ray photographic device 25B. The unit 34 calculates a three dimensional position of the target 23 based on those two-dimensional positions of the target 23.

In the memory unit 31 of the target position recognition device 26, there is prepared a projected image of the target 23 in the photographing direction of the X-ray photographic device 25A in advance as a first template image 8b. In addition, as a second template image 8c, there is prepared a projected image of the target 23 in the photographing direction of the X-ray photographic device 25B in advance.

As illustrated in FIG. 14, the two dimensional position calculation unit 33 matches the imaged image 8d of the X-ray photographic device 25A with the first template image 8b, thereby calculating the two dimensional position of the target 23 viewed from the photographing direction of the X-ray photographic device 25A. An imaged image 8e of the X-ray photographic device 25B is matched with the second template image 8c, thereby calculating a two dimensional position of the target 23 viewed from the photographing direction of the X-ray photographic device 25B. Specifically, the imaged image and the template image are compared while being moved, to calculate the similarities (for example, normalized correlation coefficients), and the position (the matching position) with the highest similarity is assumed as the two-dimensional position of the target 23. The calculated two-dimensional position of the target 23 is stored in the memory unit 31 in association with a corresponding imaged image. The process by the X-ray imaging device 25A and the process by the X-ray imaging device 25B are the same. Thus, FIG. 14 is used for the descriptions which are commonly made for both processes.

The three-dimensional position calculation unit 34 of the target position recognition device 26 calculates the three dimensional position (projection position) of the target 23, by performing reverse projection of the two-dimensional positions (projection positions) of the target 23 viewed from the photographing directions of the X-ray photographic devices 25A and 25B. The calculated three-dimensional position of the target 23 is to be displayed on the monitor 32, together with the corresponding imaged images of the X-ray photographic devices 25A and 25B. As a result, the operator can check the position of the target 23 in real time. It is possible to attain a reduction in the time for the matching process, by specifying a target search region in the imaged image displayed on the monitor 32.

The calculated three-dimensional position of the target 23 is stored in the memory unit 31, and transmitted to the irradiation control device 27. The irradiation control device 27 controls the therapeutic radiation irradiation device 24 based on the three-dimensional position of the target 23 which is received from the target position recognition device 26, to perform intercepting irradiation (specifically, to perform irradiation at a timing at which the position of the target 23 coincides with the radiation irradiation position based on treatment planning in a predetermined allowable range) or pursuit irradiation (specifically, to change the radiation irradiation position in conformity with the position of the target 23).

Descriptions will now be made to the X-ray photographic devices 25A and 25B (hereinafter simply called an X-ray imaging device) included in this embodiment. Any of the configurations common to those of the first embodiment will now be described over and over.

At the time of the moving body tracking radiation therapy, the X-ray imaging device in this embodiment calculates target position coordinates for each of the blade positions X1, X2, Y1, and Y2 in the X-ray diaphragm control board 37, to make a constant distance between the target 23 and each of the blade positions X1, X2, Y1, and Y2. The target 23 may have some characteristic structure, such as a gold marker implanted near the region of the target volume, or the bone near the target volume, or any point selected by the operator on the monitor 32. The distance between the target 23 and each blade may be set arbitrarily by the operator for each blade, within a range (the minimum X-ray irradiation range 6a at the time of recognizing the target) where the target position recognition device 26 can recognize in real time the position of the target 23.

In the conventional device, the X-ray irradiation range 6a has manually been set using a switch for controlling the blade position, while the operator is checking the display unit (monitor) 32. Thus, the operator irradiates an X-ray in a range wider than the range (the minimum X-ray irradiation range 6a at the time of recognizing the target) where the target position recognition device 26 can recognize the position of the target 23 in real time. This results in preventing the possibility that the target position recognition device 26 misses the position of the target 23, when the position of the target 23 is changed due to breathing of the patient. On the contrary, in this embodiment, the X-ray irradiation range 6a automatically follows the movement of the target 23, thus enabling to suppress the possibility of missing the target 23 even in a narrow range to be imaged and to attain a reduction in the exposure dose.

Particularly, at the time of the moving body tracking radiation therapy, by adopting the present technique, it is possible to execute the imaging within the minimum X-ray irradiation range 6a (the minimum X-ray irradiation range 6a at the time of recognizing the target) necessary for the target position recognition device 26 to recognize the position of the target 23 in real time. Thus, it is possible to reduce the exposure dose of the patients during the imaging at a time and to irradiate the therapeutic radiation over a long period of time. As a result, it is possible to improve the irradiation amount of therapeutic radiation for enabling to perform irradiation in one treatment, and to improve the efficiency of the treatment, for one patient.

Further, the target position recognition device 26 recognizes the target 23 in the minimum. X-ray irradiation range 6a at the time of recognizing the target, thereby forming the X-ray irradiation range 6a smaller than that of the conventional case. Thus, the target 23 (the matching position) can be recognized more accurately than the conventional case, and the exposure dose can further be reduced.

That is, in the conventional device, the target position recognition device 26 performs a matching process on a wide range imaged image. When the matching position is calculated, a position different from the essential target position may possibly be incorrectly recognized as a position of the target 23. In this case, the operator specifies a target search region in the imaged image displayed on the monitor 32. As a result, it is considered to attain a reduction in the time for the matching process. Needless to say, as the range of the imaged image is wide, the probability that the position of the target 23 is incorrectly recognized becomes high.

On the contrary, in this embodiment, the target 23 is recognized in the minimum X-ray irradiation range 6a at the time of recognizing the target, thereby enabling to lower the probability of incorrectly recognizing the position (matching position) corresponding to the highest similarity between the imaged image and the template image. Then, the operator specifies the target search region in the imaged image displayed on the monitor 32, thereby eliminating trouble of reducing the time for the matching process. As a result, it is possible to reduce the exposure dose of the patients. Details of this matching process will be described later.

Figure 10:
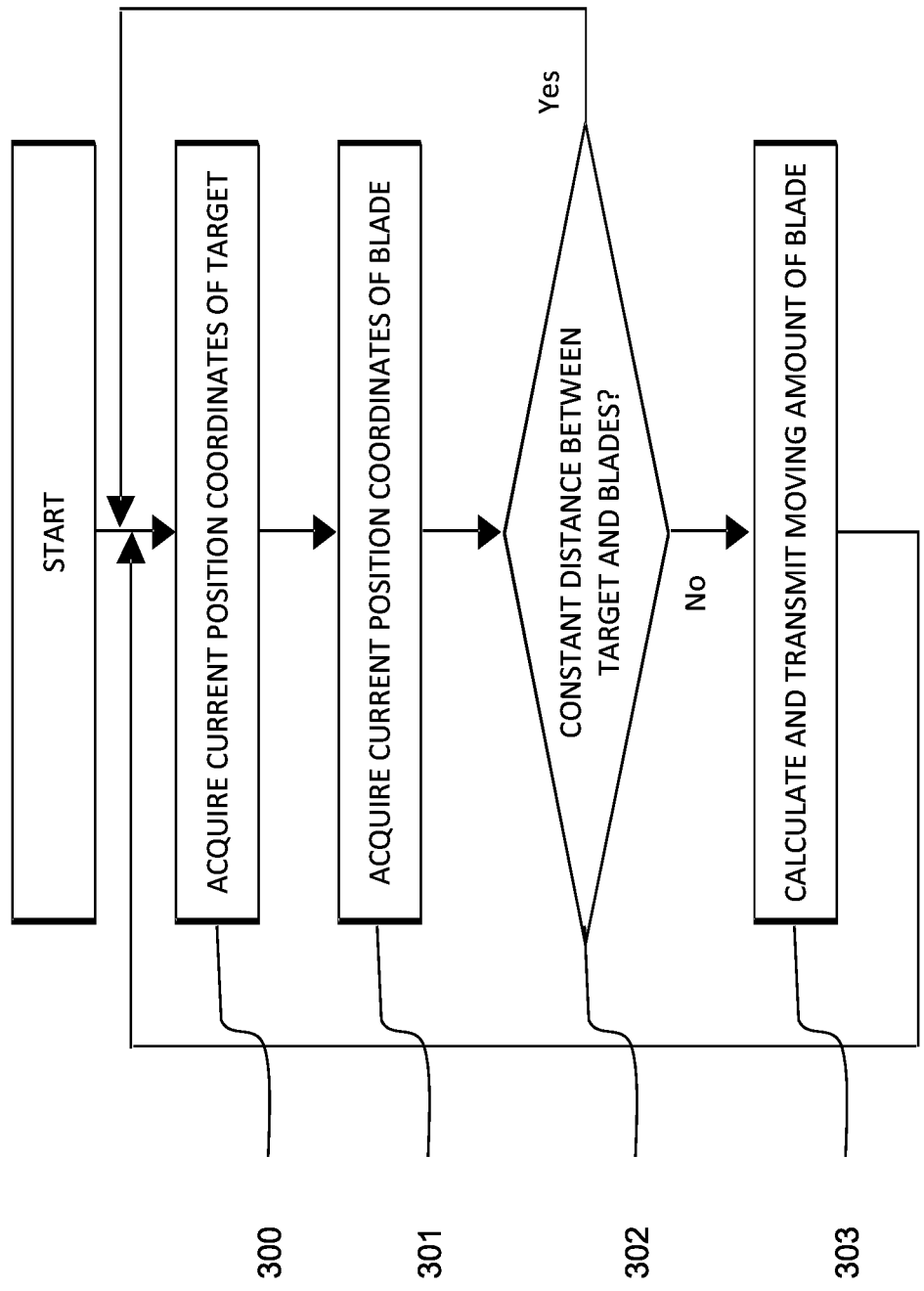
FIG. 10 is a control flow diagram of the X-ray imaging device included in the moving body tracking radiation therapy system according to the third embodiment of the present invention.

Descriptions will now be made to control procedures of the X-ray diaphragm control board 37 in the control for making a constant distance between the target 23 and each of the blade positions, using FIG. 10. FIG. 10 is a flowchart illustrating the contents of the control process of the X-ray diaphragm control board 37 in this embodiment.

In Step 300, the current position coordinates of the target 23 are calculated by the two-dimensional position calculation unit 33 and the three-dimensional position calculation unit 34, and transmitted to the memory unit 40 of the X-ray diaphragm control board 37 (hereinafter, control board 37). Then, it proceeds to Step 301, and the current position calculation unit 41 for the blade (hereinafter, current position calculation unit 41) calculates the current position coordinates of each of the blades X1, X2, Y1, and Y2 in the X-ray detection unit 2, and stores them in the memory unit 40. In Step 302, a determination unit (not illustrated) of the control board 37 determines whether the distance between the current position of the target 23 and the current position of the blade coincides with a value (the minimum X-ray irradiation range 6a at the time of recognizing the target) set by the operator, based on the data stored in the memory unit 40.

When the determination result represents coincidence, that is, when the distance between the target 23 and each of the blades is within a constant distance, it goes back to Step 300 without moving the blades. On the contrary, when the determination result represents noncoincidence, that is, when the distance between the target 23 and each of the blades is not a set value, it proceeds to Step 303. The target position calculation unit 42 for the blade (hereinafter, target position calculation unit 42) calculates a moving amount of each blade in a manner that the distance between the target 23 and each of the blades becomes a set value, and transmits a moving amount of each blade to the X-ray diaphragms 35A and 35B. Then, it goes back to Step 300. Control loop procedures which are formed from Step 300 to Step 303 are executed based on a calculation cycle of the target position recognition device and the X-ray diaphragm board 37. Thus, various control parameters, including the current position of the blade, the target position, or the moving amount are updated as needed, based on the calculation cycle. Accordingly, in this embodiment, the X-ray irradiation range 6a automatically follows the movement of the target 23, thus reducing the exposure dose of the patients.

Figure 11:
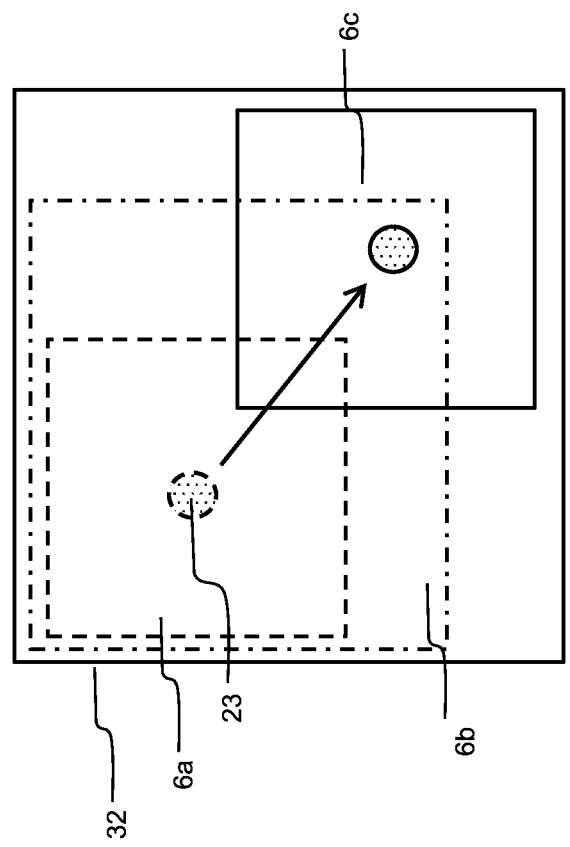
FIG. 11 is a movement image diagram of an X-ray diaphragm included in the moving body tracking radiation therapy system according to the third embodiment of the present invention.

When the target position recognition device 26 cannot adequately recognize the target 23 (for example, when the position of the target 23 is incorrectly recognized, or when it is missed), the target position recognition device 26 may continue moving the blade to the side of OPEN, until the position of the target 23 can be recognized again. In this case, the target position calculation unit 42 continuously moves the position of each blade to the side of OPEN. That is, a constant moving amount is continuously transmitted to each blade from the original irradiation range 6a illustrated in the form of a rectangle with a dotted line, and the position of the blade is set to form the X-ray irradiation range 6b shown with a one dot chain line. If the target position recognition device 26 can recognize the position of the target 23 again, the target position calculation unit 42 obtains a moving amount for realizing a constant distance between the target 23 and the position of each blade, controls the position of each blade to be in an appropriate position (the minimum X-ray irradiation range 6a at the time of recognizing the target), and sets an irradiation range 6c illustrated in the form of a rectangle with a solid line. FIG. 11 illustrates an example of this control.

In this embodiment, it is possible to perform treatment in the minimum X-ray irradiation range 6a (the minimum X-ray irradiation range 6a at the time of recognizing the target) in which the target position recognition device 26 can recognize the position of the target 23 in real time, thus enabling to remarkably reduce the exposure dose of the patients. That is, if the target position recognition device 26 misses the position of the target 23, the blade is immediately moved to the side of OPEN, and the target position recognition device 26 can recognize the position of the target 23 again. Next, after the target position recognition device 26 recognizes the position of the target 23 again, the target position calculation unit 42 controls again the blade to form the minimum X-ray irradiation range 6a at the time of recognizing the target (moves the blade to the side of CLOSE).

Figure 12:
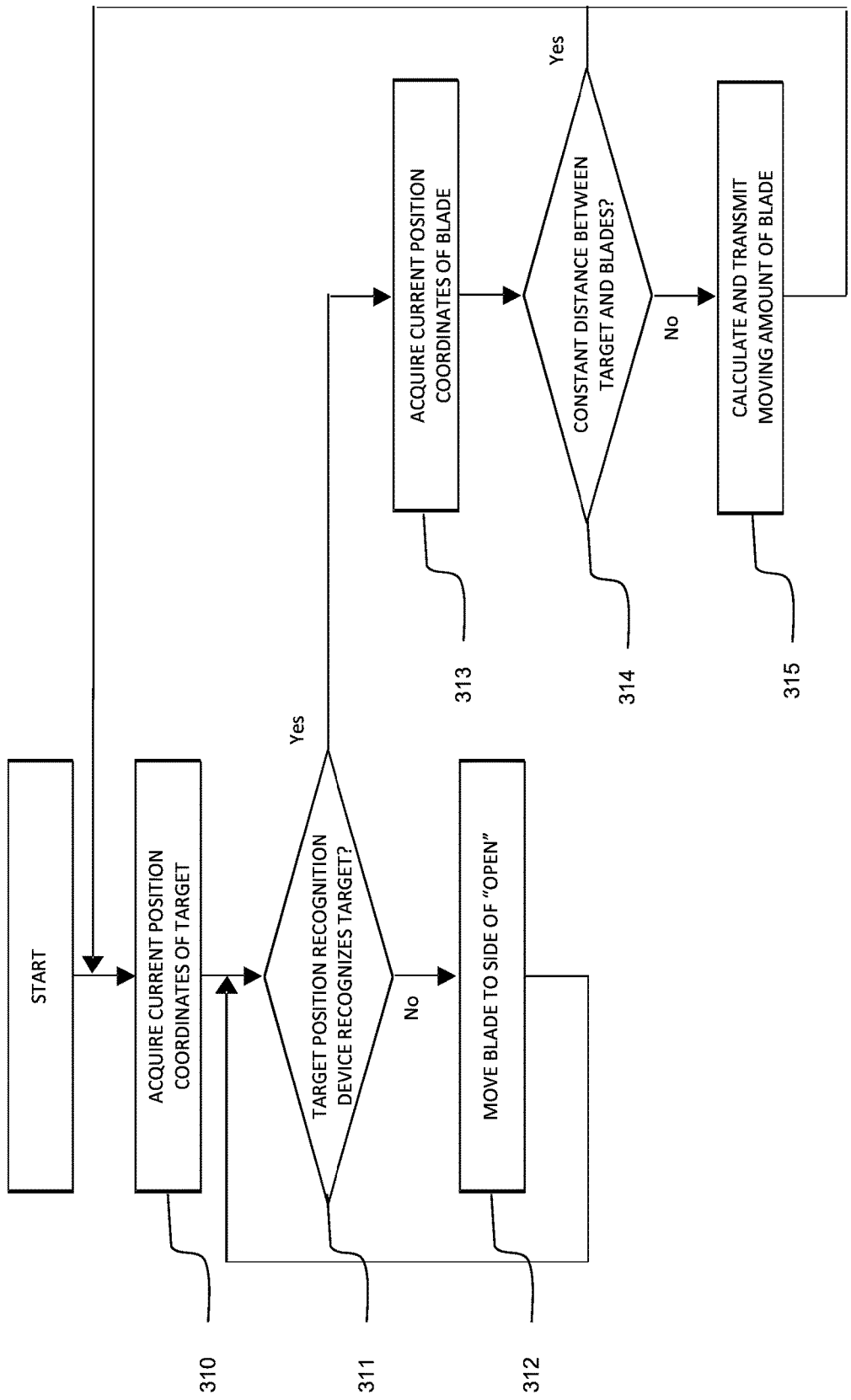
FIG. 12 is a flow diagram of X-ray imaging included in the moving body tracking radiation therapy system according to the third embodiment of the present invention.

Descriptions will now be made to the above-described matching process based on FIG. 12. In Step 310, the current position of the target 23 is calculated and stored in the memory unit 31. It can be considered that the process for detecting the position of the target 23 has previously been described using FIG. 11. In Step 311, the memory unit 31 determines whether the target 23 has been correctly recognized. Determination criteria include, for example, whether the moving speed of the target 26 or the moving amount remains within the range stored in advance in the memory unit 31, or whether the position of the target 23 remains within a range, based on an assumed region in which the target 23 would move and which is stored in the memory unit 31. In this embodiment, it can easily be detected that the target position recognition device 26 incorrectly recognizes the position of the target 23.

In the conventional device, if the target position recognition device 26 incorrectly recognizes the position of the target 23, the operator specifies the target search region in the imaged image displayed on the monitor 32, thereby attaining a reduction in the time for the matching process.

In the embodiment, if the target position recognition device 26 incorrectly recognizes the position of the target 23, the blade is immediately moved to the side of OPEN, and the target position recognition device 26 can recognize the position of the target 23 again. Thus, the operator can eliminate trouble of specifying the target search region in the imaged image displayed on the monitor 32. In addition, the target position recognition device 26 can recognize the position of the target 23 more accurately than the conventional case, thus resulting in reducing the exposure dose of the patients.

In Step 311, when the target position recognition device 26 has not correctly recognized the target 23, it proceeds to Step 312. Until the position of the target 23 can be recognized again, the target position calculation unit 42 automatically moves the position of each blade to the side of OPEN, or the operator moves each blade to the side of OPEN on the monitor 32. After this, back to Step 311, the memory unit 31 of the target position recognition device 26 continuously determines whether the target 23 has correctly been recognized.

In Step 311, when the target position recognition device 26 correctly recognizes the target 23, it proceeds to Step 313, and the current position calculation unit 41 calculates the current position coordinates of each blade in the X-ray detection unit 2 and calculates them in the memory unit 40. After this, it proceeds to Step 314, and the control board 37 determines whether the distance between the current position of the target 23 and the current position of the blade coincides with a value set by the operator. In Step 314, when the distance between the target 23 and the blade is the set value, it goes back to Step 310. It is continuously determined as to whether the target position recognition device 26 has correctly recognized the target 23, and as to whether the distance between the target 23 and the blade is the set value.

In Step 314, when the distance between the target 23 and the blade is not the set value, it proceeds to Step 315. The target position calculation unit 42 calculates the moving amount of each blade in a manner that the distance between the target 23 and the blade becomes the set value, and transmits the moving amount of each blade to the X-ray diaphragms 35A and 35B.

In Step 315, the various blade control modes listed in the first embodiment may be adopted as the method for the target position calculation unit 42 to control the position of each blade of the X-ray diaphragms 35A and 35B in a manner that the distance between the target 23 and the blade becomes the set value.

For example, in combination with the fifth mode (the memory unit 40 of the X-ray diaphragm control board 6 stores in advance the relationship between the positions of the blades which are detected by the potentiometer included in the X-ray diaphragm 5 and differences with the actual positions of the blades. The current position calculation unit 41 for the blade displays the position of each blade on the monitor 8 or 9, and the target position calculation unit 42 for the blade transmits the target position coordinates for each blade to the X-ray diaphragm 5. At this time, the image processing device 7 or the X-ray diaphragm control board 6 automatically corrects the above error.) described in the first embodiment, it is possible to reduce a stop error of the blade due to a quantization error of the potentiometer or hysteresis, and the X-ray irradiation range 6a can accurately follow the movement of the target 23. As a result, it is possible to attain a reduction of the exposure dose of the patients.

After this, back to Step 310, it is continuously determined that the target position recognition device 26 correctly recognizes the target 23, and that the distance between the target and the blade is the set value.

As illustrated in FIG. 14, the imaged image (a target peripheral image) which is controlled to realize the constant distance between the target 23 and the position of each of the blades is superimposed with the template image 8b or 8c stored in the memory unit 40, and is displayed. This superimposed image is transmitted to the memory unit 31, and the superimposed image and the template image are matched. As a result, it is possible to form a mode (eighth mode) for calculating two-dimensional positions of the target 23 viewed from the photographing directions of the X-ray photographic devices 25A and 25B.

In this embodiment, the target position recognition device 26 matches the superimposed image with the template image, and the two-dimensional position of the target 23 viewed from the photographing directions of the X-ray photographic devices 25A and 25B is calculated. By so doing, the X-ray irradiation range 6a is made further small, and the target position recognition device 26 can further correctly recognize the target 23. As a result, it is possible to reduce the exposure dose of the patients.

Figure 13:
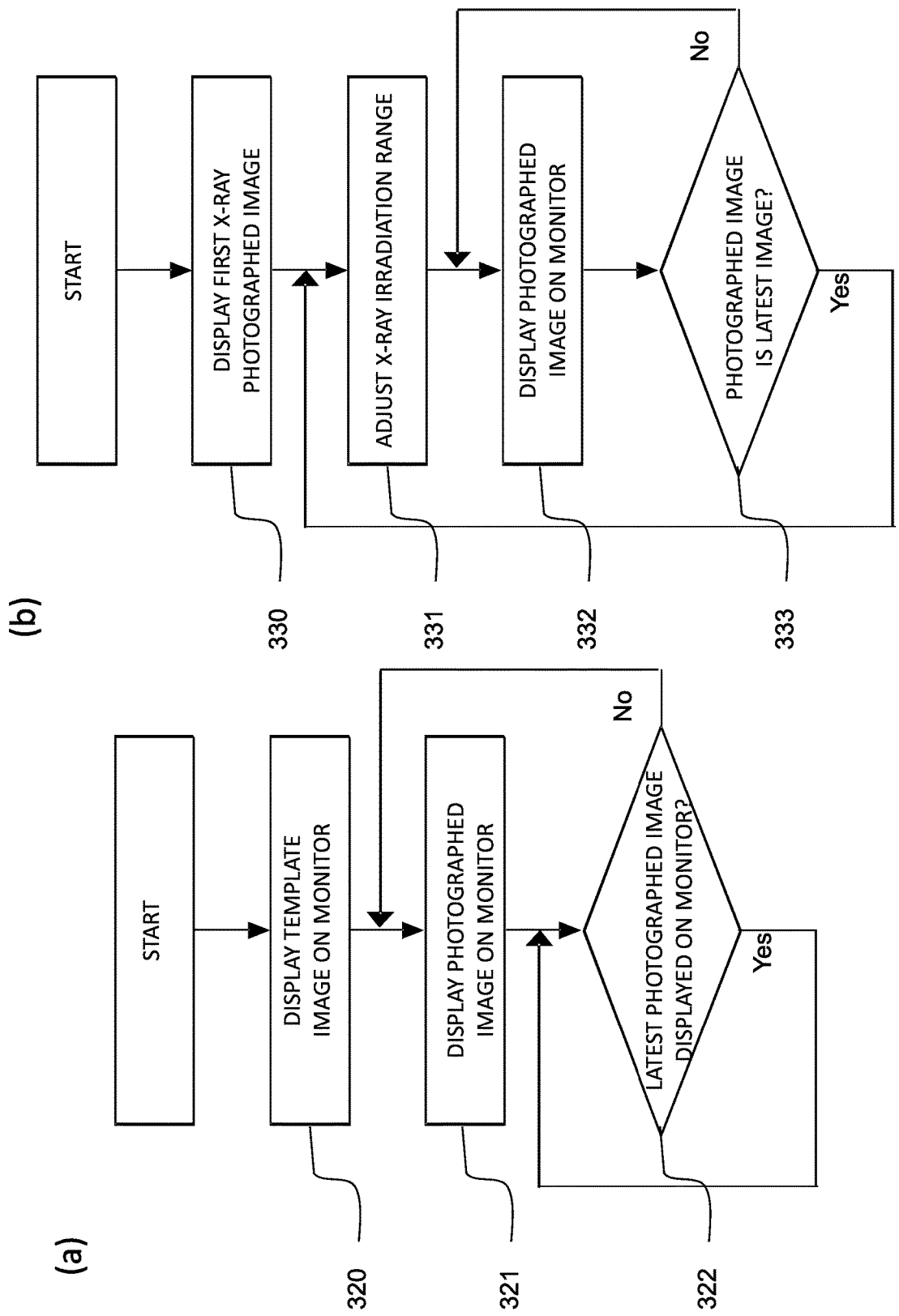
FIG. 13 is a flow diagram of a matching process in the X-ray imaging included in the moving body tracking radiation therapy system according to the third embodiment of the present invention.

Next, the control procedures of this control mode will now be described using FIG. 13(a). FIG. 13(a) is a flowchart illustrating the contents of a control process of the X-ray diaphragm control board 37 in this embodiment.

In Step 320, the template image stored in the memory unit 40 of the control board 37 is displayed on the monitor 32. After this, it proceeds to Step 321 in which the imaged image received from the X-ray detection devices 29A and 29B is displayed. This image is superimposed with the template image displayed on the monitor 32 in Step 320. After this, it proceeds to Step 322, and the target position recognition device 26 determines whether the imaged image displayed on the monitor 32 is the latest image.

In Step 322, when the imaged image displayed on the monitor 32 is not the latest image, it goes back to Step 321. The target position recognition device 26 receives the latest imaged image from the X-ray detection devices 29A and 29B. In Step 322, when the imaged image displayed on the monitor 32 is the latest image, the target position recognition device 26 determines whether the imaged image continuously displayed on the monitor 32 is the latest image.

In the control mode, the target position recognition device 26 recognizes the position of the target 23, using the superimposed image displayed on the monitor 32 in Step 322. In this case, consideration is given to a mode for using previous X-ray imaged images photographed by the X-ray photographic devices 25A and 25B, instead of the template images 8b and 8c stored in the memory unit 40, as images of the subject 22 displayed on the monitor 32 in Step 320.

The control procedures of this control mode will now be described using FIG. 13(b). FIG. 13(b) is a flowchart illustrating the contents of a control process of the control board 37 in this embodiment.

In Step 330, the X-ray photographic devices 25A and 25B photograph the subject 22, and transmit photographed data to the memory unit 31 and the memory unit 40. The target position recognition device 26 reads data stored in the memory unit 31, and displays it on the monitor 32 as a first imaged image.

After this, it proceeds to Step 331. To make a constant distance between the target 23 and each of the positions of the blades, the movement of the blade is automatically or manually controlled to adjust the X-ray irradiation range 6a (a target peripheral image).

In Step 331, for the distance between the target 23 and each of the blades to be the set value, the operator may specify the target position of each blade, using the various blade control modes listed in the first embodiment.

After this, it proceeds to Step 322, and the target position recognition device 26 displays the imaged image (a target peripheral image), received from the X-ray detection devices 29A and 29B and superimposed with the first imaged image displayed on the monitor 32, and determines whether the imaged image displayed on the monitor 32 is the latest image. In Step 333, when the imaged image displayed on the monitor 32 is not the latest image, it goes back to Step 332. The target position recognition device 26 and the control board 37 receive the latest imaged image from the X-ray detection devices 29A and 29B.

In Step 333, when the imaged image (a target peripheral image) displayed on the monitor 32 is the latest image, the target position recognition device 26 determines whether the imaged image continuously displayed on the monitor 32 is the latest image. In this control mode, the target position recognition device 26 recognizes the position of the target 23 using the superimposed image displayed on the monitor 32 in Step 332.

At the time of the moving body tracking radiation therapy, in the X-ray imaging device of this embodiment, the target position calculation unit 42 for the blade in the control board 37 calculates target position coordinates of the position of each blade to control the position of each blade, in a manner that a constant distance is made between the target 23 and each of the positions of the blades X1, X2, Y1, and Y2. At this time, to reduce the X-ray exposure dose of the patients, the distance between the target 23 and the position of each of the blades X1, X2, Y, and Y2 is set to form the necessary minimum X-ray irradiation range 6a (the minimum X-ray irradiation range 6a at the time of recognizing the target) that the target position recognition device 26 can recognize the position of the target in real time.

If the target position recognition device 26 misses (incorrectly recognizes) the position of the target 23, the blade is immediately moved to the side of OPEN, and the target position recognition device 26 can recognize the position of the target 23 again. Next, after the target position recognition device 26 recognizes the position of the target 23 again, the target position calculation unit 42 controls the blade again to form the minimum X-ray irradiation range 6a at the time of recognizing the target (moves the blade to the side of CLOSE).

The memory unit 31 determines that the target position recognition device 26 incorrectly recognizes the position of the target 23, based on some criterion whether, for example, the moving speed or moving amount of the target 26 remains in the range stored in advance in the memory unit 31, or whether the position of the target 23 remains within a range, based on an assumed region in which the target 23 would move and which is stored in the memory unit 31. If the target position recognition device 26 incorrectly recognizes the position of the target 23, the blade is immediately moved to the side of OPEN, and the target position recognition device 26 can recognize the position of the target 23 again. Alternatively, the operator specifies a target search region in the imaged image displayed on the monitor 32, thereby the target position recognition device 26 can recognize the position of the target 23 again.

By the above functions, in this embodiment, as compared to the conventional cases, the target position recognition device 26 can more accurately recognize the position of the target 23, thereby resulting in reducing the exposure dose of the patients.

In general (may somehow differ, depending on the position or form of the target), as the imaging range gets small, the target position recognition device 26 can correctly recognize the position of the target 23. However, depending on the position or form of the target, the target may sometimes accurately be recognized, if the imaged image has a wide range. In this case, the imaged image of the X-ray photographic devices 25A and 25B is displayed in a form superimposed with the template image stored in the memory unit 31 of the target position recognition device 26.

The target position recognition device 26 matches the superimposed image with the template image, and calculates a two-dimensional position of the target 23 viewed from the photographing directions of the X-ray photographic devices 25A and 25B. As a result, it is possible to make the X-ray irradiation range 6a further smaller. In addition, the target position recognition device 26 can more accurately recognize the target 23.

When the target position recognition device 26 misses the target 23, for the target position recognition device 26 to be able to recognize again the position of the target 23, the blade is automatically or manually moved to the side of OPEN. After the target position recognition device 26 recognizes the position of the target 23 again, it automatically or manually moves each blade again to the side of CLOSE by a predetermined amount. To make a constant distance between the target 23 and the position of each of the blades, the target position calculation unit 42 controls the position of each of the blades.

While each blade is controlled to follow the movement of the target 23, each of the blades may be controlled in a combination of any of the various modes listed in the first embodiment. For example, while specifying the side of OPEN or CLOSE for the position of each blade which is displayed or displayed by simulation on the monitor 32, it is possible to combine a mode for continuously keeping moving the blade in the specified direction. When this mode is combined, when the target position recognition device 26 misses the target 23, the target position recognition device 26 can again recognize the target 23 in a short period of time. As a result, the memory unit 31 of the target position recognition device 26 can accurately recognize the target, and it can be expected to reduce the X-ray exposure dose of the patients.

LIST OF REFERENCE SIGNS

1 X-ray Tube
2 X-ray Detection Unit
3 Subject
4 C-Arm
5 X-ray Diaphragm
6 X-ray Diaphragm Control Board
7 Image Processing Device
8, 9 Display Unit (Monitor)
15 Therapeutic Radiation Irradiation Device
16 Irradiation Control Device
17 Laser Marker
18 Therapy Table
20 Communication Unit
22 Subject
23 Target
24 Therapeutic Radiation Irradiation Device
25A, 25B X-ray Photographic Device
26 Target Position Recognition Device
27 Irradiation Control Device
28A, 28B X-ray Tube
29A, 29B X-ray Detection Unit
31 Memory Unit
32 Display Unit (Monitor)
33 Two-Dimensional Position Calculation Unit
34 Three-Dimensional Position Calculation Unit
35A, 35B X-ray Diaphragm
36 Recognition Result Output Device
37 X-ray Diaphragm Control Board
39 Communication Unit
40 Memory Unit
41 Blade Current Position Calculation Unit
42 Blade Target Position Calculation Unit
110 Radiation Therapy Device
120 Moving Body Tracking Radiation Therapy Device

The invention claimed is:

1. A radiation therapy system, comprising:
an X-ray imaging device;
a radiation therapy device for irradiating radiation for treatment; and
a control device which is connected to the X-ray imaging device or the radiation therapy device,
wherein the X-ray imaging device includes:
an X-ray generation unit,
an X-ray detection unit which detects an X-ray irradiated from the X-ray generation unit, thereby acquiring a transmission image of a subject,
a movable X-ray diaphragm unit, including a blade, which adjusts an irradiation range of an X-ray irradiated from the X-ray generation unit,
wherein the movable X-ray diaphragm unit includes:
an X-ray shielding unit which is configured with a plurality of members,
a driver for the X-ray shielding unit, and
a position detection detector for acquiring a position of the X-ray shielding unit,
wherein the control device includes a display for displaying the transmission image of the subject based on an output of the X-ray detection unit and a simulation image when the X-ray shielding unit based on an output of the position detector is projected on the X-ray detection unit, and
wherein the control device is configured to:
periodically output an instruction to perform imaging to the X-ray imaging device, acquires images of a target, and displays the acquired images of the target on the display,
determine whether a distance between a position of the target and a simulated image matches a preset value,
calculate a moving amount of a blade of the movable X-ray diaphragm unit in such a manner that the distance between the position of the target and the simulated image matches the preset value upon determining that the distance between the position of the target and the simulated image does not match the preset value, and
output an instruction for moving the X-ray shielding unit toward the position of the target.

2. The radiation therapy system according to claim 1, wherein the control device receives an instruction to set a distance between the images of the markers and the simulation image.

3. The radiation therapy system according to claim 1, wherein the control device extends, when the markers are moved outside the irradiation range of an X-ray formed by the X-ray shielding unit to acquire the images of the markers, the irradiation range of an X-ray until the images of the markers are acquired.

4. The radiation therapy system according to claim 1, wherein the control device
stores a specified region set in advance in the transmission image,
allows irradiation of radiation by the radiation therapy device, when the periodically acquired images of the markers are included in the specified region, and
controls to stop irradiation of radiation performed by the radiation therapy device, when the periodically acquired images of the markers deviate from the specified region.

5. The radiation therapy system according to claim 1, wherein the control device
includes a memory unit which stores an opening state of the blade of the movable X-ray diaphragm unit,
reads a state regarding a previous opening state of the blade movable X-ray diaphragm unit from the memory unit, and
outputs an instruction for reproducing the previous opening state of the movable X-ray diaphragm unit, to the driver.

6. A radiation therapy system comprising:
an X-ray imaging device including an X-ray generation unit;
a radiation therapy device for irradiating radiation for treatment;
a control device which is connected to the X-ray imaging device or the radiation therapy device;
an X-ray detection unit, which detects an X-ray irradiated from the X-ray generation unit, thereby acquiring a transmission image of a subject; and a movable X-ray diaphragm unit which adjusts an irradiation range of an X-ray irradiated from the X-ray generation unit, wherein the movable X-ray diaphragm unit includes:

an X-ray shielding unit which is configured with a plurality of members, a driver for the X-ray shielding unit, and a position detection detector for acquiring a position of the X-ray shielding unit, wherein the control device:

acquires a current position of the prearranged target, determines whether the target is recognized, moves respective positions of a plurality of blades of the moveable X-ray diaphragm unit to an open side until a position of the target can be recognized if the target is not recognized, calculates the current position coordinates of each blade if the target is recognized, determines whether the distance between the current position of the target and the current position of each blade matches a value set by an operator, continuously determines that the target is recognized and that the distance between the target and each blade is a set value when the distance between the target and each blade is the set value, and calculates the moving amount of each blade in such manner that the distance between the target and each blade becomes the set value and transmits the movement amount of each blade to the driver if the distance between the target and each blade is not the set value.

* * * * *